US 6,747,061 B2
Jun. 8, 2004

(12) United States Patent
Medford et al.

(10) Patent No.: US 6,747,061 B2
(45) Date of Patent: Jun. 8, 2004

(54) N-SUBSTITUTED DITHIOCARBAMATES FOR THE TREATMENT OF BIOLOGICAL DISORDERS

(75) Inventors: Russell M. Medford, Atlanta, GA (US); Uday Saxena, Atlanta, GA (US); Lee K. Hoong, Suwanee, GA (US); Patricia K. Somers, Fort Collins, CO (US)

(73) Assignee: AtheroGenics, Inc., Alpharetta, GA (US)

( * ) Notice: Subject to any disclaimer, the term of this patent is extended or adjusted under 35 U.S.C. 154(b) by 0 days.

(21) Appl. No.: 09/815,244

(22) Filed: Mar. 21, 2001

(65) Prior Publication Data

US 2003/0176496 A1 Sep. 18, 2003

Related U.S. Application Data

(60) Provisional application No. 60/190,790, filed on Mar. 21, 2000.

(51) Int. Cl.$^7$ .................. A61K 31/34; C07D 307/02
(52) U.S. Cl. ........................ 514/471; 549/496
(58) Field of Search .............. 549/493, 496; 514/471

(56) References Cited

U.S. PATENT DOCUMENTS

| 3,875,170 A | 4/1975 | Matsumoto et al. ... 260/243.69 |
| 4,120,966 A | 10/1978 | Brown et al. ............. 424/263 |
| 4,120,972 A | 10/1978 | Brown et al. ............. 424/273 |
| 4,166,866 A | 9/1979 | Wight et al. ............. 424/300 |
| 4,173,644 A | 11/1979 | Brown et al. ............. 424/270 |
| 4,202,832 A | 5/1980 | Fischer et al. ............. 260/455 |
| 4,594,238 A | 6/1986 | Borch ........................ 424/10 |
| 5,002,755 A | 3/1991 | Mitchell et al. ............. 424/10 |
| 5,187,193 A | 2/1993 | Borch et al. ............. 514/476 |
| 5,294,430 A | 3/1994 | Borch et al. ............. 424/10 |
| 5,344,842 A | 9/1994 | Missbach ................. 514/342 |
| 5,380,747 A | 1/1995 | Medford et al. ........... 514/423 |
| 5,563,159 A | 10/1996 | Kusaba et al. ............. 514/346 |
| 5,750,351 A | 5/1998 | Medford et al. ........... 435/7.21 |
| 5,773,209 A | 6/1998 | Medford et al. ........... 435/7.24 |
| 5,783,596 A | 7/1998 | Medford et al. ........... 514/423 |
| 5,792,787 A | 8/1998 | Medford et al. ........... 514/423 |
| 5,807,884 A | 9/1998 | Medford et al. ........... 514/423 |
| 5,811,449 A | 9/1998 | Medford et al. ........... 514/423 |
| 5,821,260 A | 10/1998 | Medford et al. ........... 514/423 |
| 5,846,959 A | 12/1998 | Medford et al. ........... 514/165 |
| 5,877,203 A | 3/1999 | Medford et al. ........... 514/703 |

FOREIGN PATENT DOCUMENTS

| EP | 0617036 | * 9/1994 |
| JP | 49135942 A2 | 12/1974 |
| JP | 51105016 A2 | 9/1976 |
| JP | 55015457 A2 | 2/1980 |
| US | WO 95/30415 | 11/1995 |
| WO | WO 99/01118 | 1/1999 |
| WO | WO 00/00192 | 1/2000 |

OTHER PUBLICATIONS

Miles P. Hacker, et al., Effect of Disulfiram (Tetraethylthiuram Disulfide) and Diethyldithiocarbamate on the Bladder Toxicity and Antitumor Activity of Cyclophosphamide in Mice; Cancer Research, Nov. 1982, pp. 4490–4494, vol. 42, No. 11.

* cited by examiner

Primary Examiner—Alan L. Rotman
Assistant Examiner—Binta Robinson
(74) Attorney, Agent, or Firm—Sherry M. Knowles, Esq.; King & Spalding LLP; Alan L. Scrivner, Esq.

(57) ABSTRACT

N-substituted dithiocarbamate esters, pharmaceutical compositions containing them, and methods of treating hyperproliferative disorders such as cancer by administering the N-substituted dithiocarbamate esters.

59 Claims, 4 Drawing Sheets

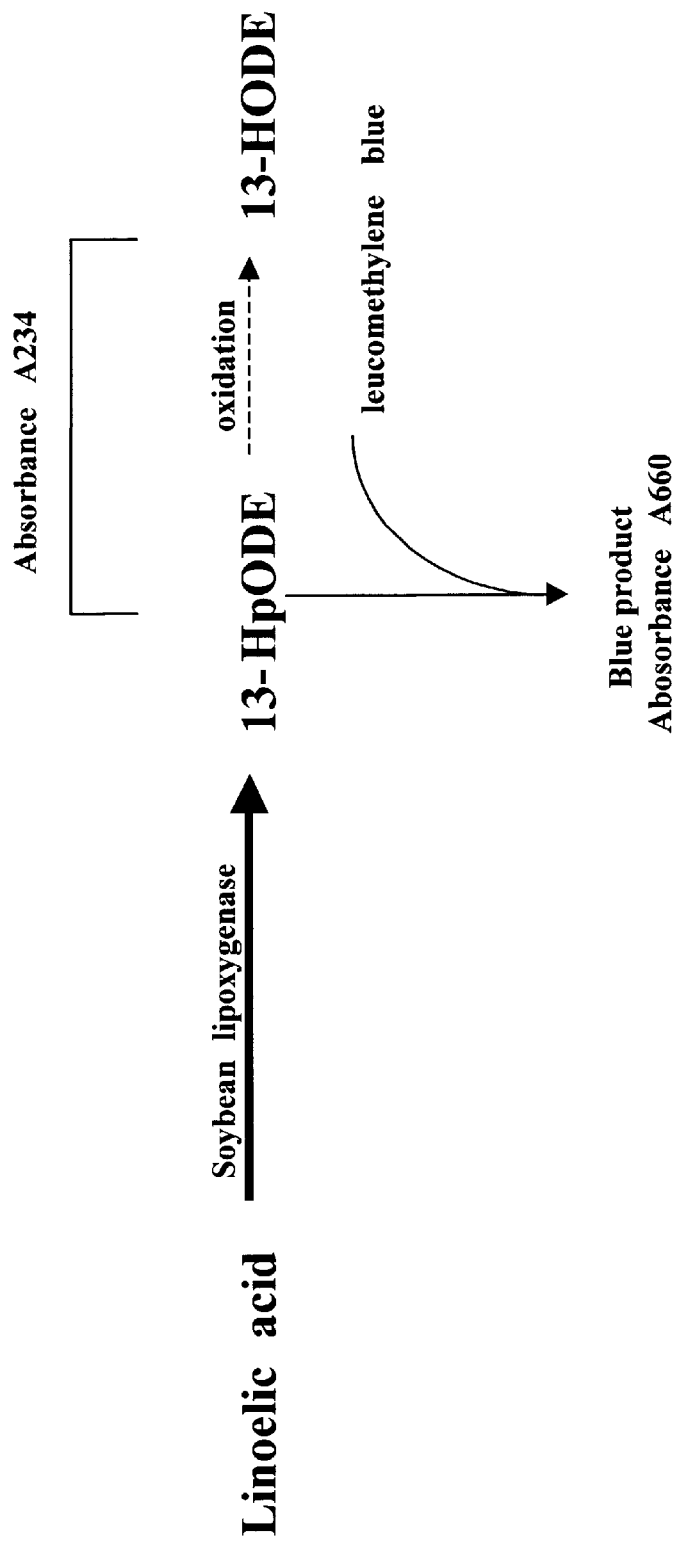
Figure 2: Leucomethylene Blue Assay (LMB)

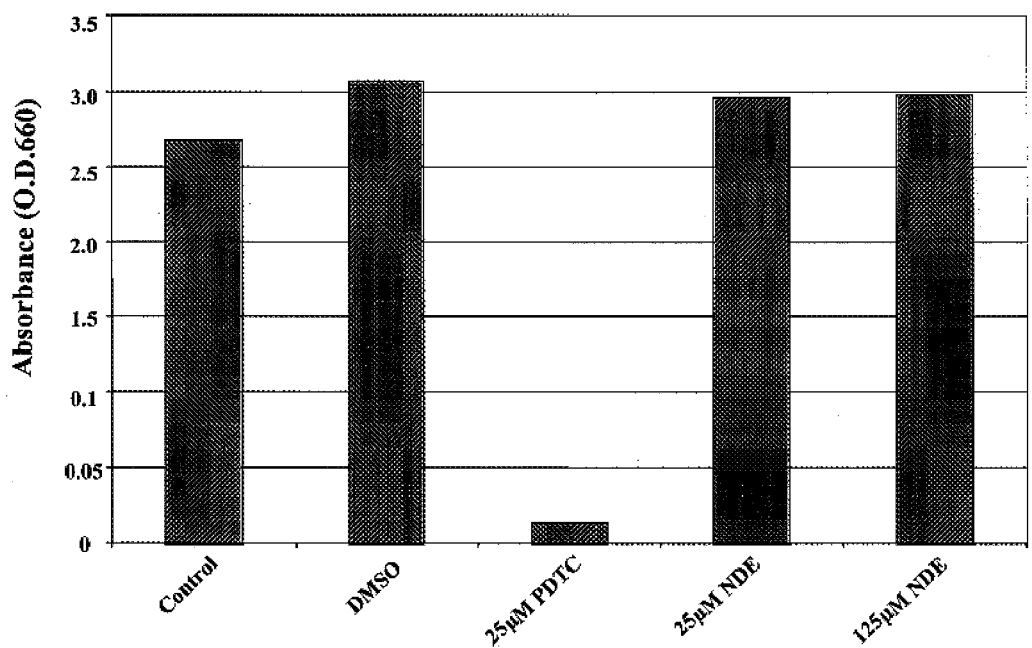
Figure 3: NDE is not an antioxidant as determined by the LMB assay

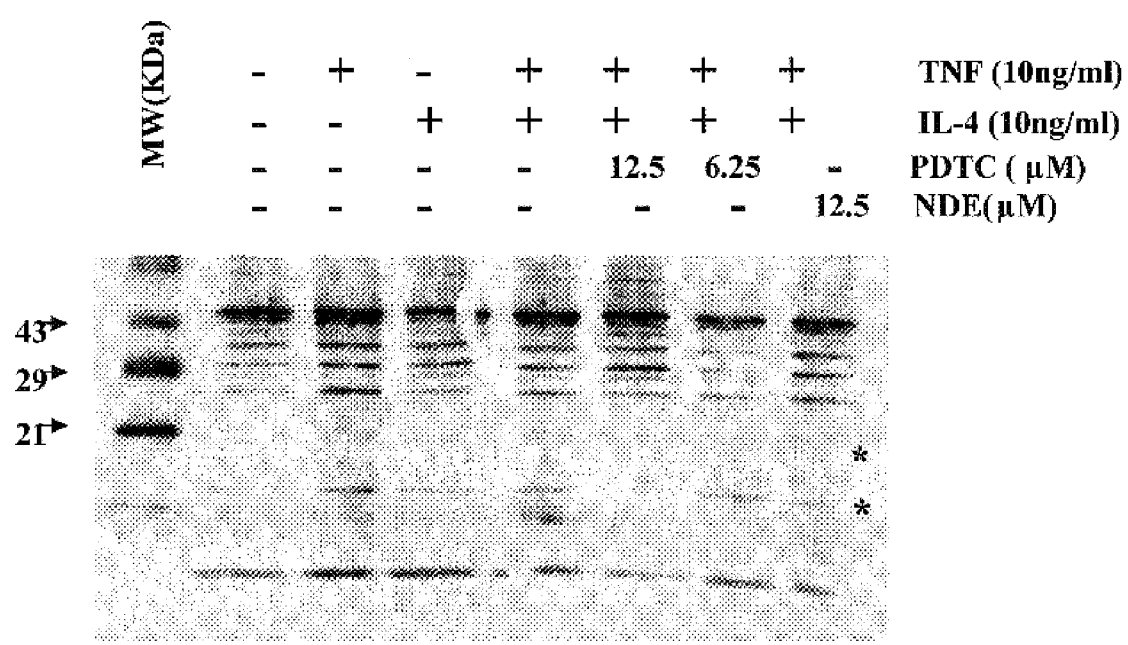
Figure 4: PDTC but not NDE inhibited cytokine induced oxidatively modified proteins in NHBE cells as measured by the OxyBlot oxidized protein detection kit

N-SUBSTITUTED DITHIOCARBAMATES FOR THE TREATMENT OF BIOLOGICAL DISORDERS

RELATED APPLICATIONS

This application claims priority to U.S. Provisional Application No. 60/190,790, filed Mar. 21, 2000.

FIELD OF THE INVENTION

The present invention describes N-substituted dithiocarbamate esters and their use in the treatment of biological disorders. The N-substituted dithiocarbamate esters are particularly useful in the treatment of hyperproliferative conditions such as cancer. They can also be used in the treatment of VCAM-1 mediated conditions such as cardiovascular disorders and inflammatory diseases.

BACKGROUND OF THE INVENTION

A wide range of disorders involve the hyperproliferation of cells, ranging from psoriasis to benign and malignant tumors. These disorders are generally caused by a loss of control over normal cell growth, differentiation, or the process of programmed cell death (apoptosis). Many of the abnormalities that underlie these disorders, particularly cancer, occur at the genetic level. Antineoplastic agents (also known as cytotoxic agents) are often used in the treatment of hyperproliferative conditions. Therapy with antineoplastic agents is successful in the treatment of a number of malignant conditions; however, in most it is used to palliate the symptoms and to prolong life in patients with advanced disease.

Cancer is a class of tumors that is characterized by invasiveness and metastasis. It is possible to recur after attempted removal, and causes death unless adequately treated. *Stedman's Medical Dictionary*, 25th Edition Illustrated, Williams & Wilkins, 1990. Approximately 1.2 million Americans are diagnosed with cancer each year, 8,000 of which are children. In addition, 500,000 Americans die from cancer each year in the United States alone. Specifically, lung and prostate cancer are the top cancer killers for men while lung and breast cancer are the top cancer killers for women. It is estimated that cancer-related costs account for about 10 percent of the total amount spent on disease treatment in the United States. *CNN Cancer Facts*, http://www.cnn.com/HEALTH/9511/conquer_cancer/facts/index.html, page 2 of 2, Jul. 18, 1999.

Although a variety of approaches to cancer therapy (e.g., surgical resection, radiation therapy, and chemotherapy) are available and have been used for many years, cancer remains one of the leading causes of death in the world. This is due in part to the fact that the therapies themselves cause significant toxic side-effects and re-emergence is common.

Antineoplastic agents have been described extensively in a number of texts, including Martindale, *The Extra Pharmacopoeia*, 31st Edition, Royal Pharmaceutical Society (1996).

Antineoplastic agents include:
(i) antifolates;
(ii) antimetabolites (including purine antimetabolites, cytarabine, fudarabine, floxuridine, 6-mercaptopurine, methotrexate, 5-fluoropyrimidine, including 5-fluorouracil, cytidine analogues such as β-L-1,3-dioxolanyl cytidine and 6-thioguanine);
(iii) hydroxyurea;
(iv) mitotic inhibitors (including CPT-11, Etoposide(VP-21)), taxol, and vincristine,
(v) alkylating agents (including but not limited to busulfan, chlorambucil, cyclophosphamide, ifofamide, mechlorethamine, melphalan, and thiotepa);
(vi) nonclassical alkylating agents, platinum containing compounds, bleomycin, anti-tumor antibiotics, anthracycline, anthracenedione, topoisomerase 11 inhibitors, hormonal agents (including but not limited to corticosteroids (dexamethasone, prednisone, and methylprednisone); and
(v) androgens such as fluoxymesterone and methyltestosterone, estrogens such as diethylstilbesterol, antiestrogens such as tamoxifen, LHRH analogues such as leuprolide, antiandrogens such as flutamide, aminoglutethimide, megestrol acetate, and medroxyprogesterone), asparaginase, carmustine, lomustine, hexamethyl-melamine, dacarbazine, mitotane, streptozocin, cisplatin, carboplatin, levamasole, and leucovorin.

A more comprehensive list of antineoplastic agents includes Aceglatone; Aclarubicin; Altretamine; Aminoglutethimide; 5-Aminogleavulinic Acid; Amsacrine; Anastrozole; Ancitabine Hydrochloride; 17-1A Antibody; Antilymphocyte Immunoglobulins; Antineoplaston A10; Asparaginase; Pegaspargase; Azacitidine; Azathioprine; Batimastat; Benzoporphyrin Derivative; Bicalutamide; Bisantrene Hydrochloride; Bleomycin Sulphate; Brequinar Sodium; Broxuridine; Busulphan; Campath-IH; Caracemide; Carbetimer; Carboplatin; Carboquone; Carmofur; Carmustine; Chlorambucil; Chlorozotocin; Chromomycin; Cisplatin; Cladribine; Corynebacterium parvum; Cyclophosphamide; Cyclosporin; Cytarabine; Dacarbazine; Dactinomycin; Daunorubicin Hydrochloride; Decitabine; Diaziquone; Dichlorodiethylsulphide; Didemnin B.; Docetaxel; Doxifluridine; Doxorubicin Hychloride; Droloxifene; Echinomycin; Edatrexate; Elliptinium; Elmustine; Enloplatin; Enocitabine; Epirubicin Hydrochloride; Estramustine Sodium Phosphate; Etanidazole; Ethoglucid; Etoposide; Fadrozole Hydrochloride; Fazarabine; Fenretinide; Floxuridine; Fludarabine Phosphate; Fluorouracil; Flutamide; Formestane; Fotemustine; Gallium Nitrate; Gencitabine; Gusperimus; Homoharringtonine; Hydroxyurea; Idarubicin Hydrochloride; Ifosfamide; Ilmofosine; Improsulfan Tosylate; Inolimomab; Interleukin-2; Irinotecan; JM-216; Letrozole; Lithium Gamolenate; Lobaplatin; Lomustine; Lonidamine; Mafosfamide; Melphalan; Menogaril; Mercaptopurine; Methotrexate; Methotrexate Sodium; Miboplatin; Miltefosine; Misonidazole; Mitobronitol; Mitoguazone Dihydrochloride; Mitolactol; Mitomycin; Mitotane; Mitozanetrone Hydrochloride; Mizoribine; Mopidamol; Multialchilpeptide; Muromonab-CD3; Mustine Hydrochloride; Mycophenolic Acid; Mycophenolate Mofetil; Nedaplatin; Nilutamide; Nimustine Hydrochloride; Oxaliplatin; Paclitaxel; PCNU; Penostatin; Peplomycin Sulphate; Pipobroman; Pirarubicin; Piritrexim Isethionate; Piroxantrone Hydrochloride; Plicamycin; porfimer Sodium; Prednimustine; Procarbazine Hydrochloride; Raltitrexed; Ranimustine; Razoxane; Rogletimide; Roquinimex; Sebriplatin; Semustine; Sirolimus; Sizofiran; Sobuzoxane; Sodium Bromebrate; Sparfosic Acid; Sparfosate Sodium; Sreptozocin; Sulofenur; Tacrolimus; Tamoxifen; Tegafur; Teloxantrone Hydrochloride; Temozolomide; Teniposide; Testolactone; Tetrasodium Meso-tetraphenylporphinesulphonate; Thioguanine; Thioinosine; Thiotepa; Topotecan; Toremifene; Treosulfan; Trimetrexate; Trofosfamide; Tumor Necrosis Factor; Ubenimex; Uramustine; Vinblastine Sulphate; Vincristine Sulphate; Vindesine Sulphate; Vinorelbine Tartrate; Vorozole; Zinostatin; Zolimomab Aritox; and Zorubicin Hydrochloride.

For about four decades, the antimetabolite 5-fluorouracil (5-FU), and nucleosides which include this base (e.g., 5-fluoro-2'-deoxyuridine or FdUrd), have remained among the few "standard" drugs effective against solid tumors in man. 5-Fluorouracil is used mainly for the treatment of colorectal, ovarian, renal, breast and head and neck cancers. 5-Fluoro-2'-deoxyuridine is used for the treatment of solid tumors, including hepatic metastases of advanced gastrointestinal adenocarcinomas, renal cell carcinomas, advanced ovarian cancer, and squamous cell carcinomas of the head and neck. The clinical utility of the fluoropyrimidines is limited by the host-toxicity induced by the administration of these compounds. Manifestations of the host-toxicity of the fluoropyrimidines include mainly gastrointestinal epithelial ulceration, myelosuppression and, to a lesser extent, cardiotoxicities, hepatotoxicities and neurotoxicities. A population of cancer patients is intolerant to treatment with 5-fluorouracil and 5-fluoro-2'-deoxyuridine. Moreover, it has also been shown that cancers, treated with fluoropyrimidines, become resistant, i.e., develop tolerance towards these drugs.

Colorectal cancer (CRC) is a multi-step process resulting from the accumulation of mutations in clonal populations of colonocytes. Mutations of the p53 tumor suppressor gene are a relatively late, yet common event in the pathogenesis of colorectal cancer, occurring in over 80% of late adenomas and carcinomas (Fearon, et al., FASEB J. 6, 2789 (1992); Srivastarva, et al., Contemp. Oncol. April 63 (192); Kline, et al., Cancer (Phila. 73, 28 (1994). Conventional therapy for advanced disease, such as cytotoxic chemotherapy and gamma-irradiation, induce DNA damage in proliferating cells. This damage, through undefined mechanism(s), signals the induction of p53, which, in turn, leads to inhibition of cellular proliferation by induction of $G_1$ cell cycle arrest and, in some instances, apoptosis. Thus, tumors lacking functional p53 are frequently refractory to such therapies (S. C. Righetti et al., *Cancer Res.* 56, 689 (1996); J. S. Kovack et al., *Proc. Natl. Acad, Sci.* U.S.A. 93, 1093 (1996)), emphasizing the importance of developing treatments for advanced colorectal cancer that do not rely on functional p53.

The most effective single chemotherapeutic agent for advanced colorectal cancer to date remains 5-FU. The active metabolite of 5-FU, 5-fluorodeoxyuridine-5'-monophosphate (FdUMP), forms a complex with thymidylate synthase (TS) in the presence of reduced folate, thereby inhibiting enzyme activity, and depleting precursors for DNA synthesis. 5-FU is also incorporated into RNA, altering its processing and function, although how this correlates with cytotoxicity is unknown. Previous data suggest that 5-FU can utilize both p53-dependent and independent pathways (Pritchard, et al., Pharmacol. Ther. 72, 149 (1996)), although a loss of p53 function dramatically reduces 5-FU efficacy (B. Cohen et al., Cancer (Phila.) 67, 1859 (1991); Advanced Cancer Meta-Analysis Project, J. Clin. Oncol. 10, 896 (1992)).

VCAM-1

Adhesion of leukocytes to the endothelium represents a fundamental, early event in a wide variety of inflammatory conditions, including atherosclerosis, autoimmune disorders and bacterial and viral infections. Leukocyte recruitment to the endothelium is started when inducible adhesion molecule receptors on the surface of endothelial cells interact with counterreceptors on immune cells. Vascular endothelial cells determine which type of leukocytes (monocytes, lymphocytes, or neutrophils) are recruited, by selectively expressing specific adhesion molecules, such as vascular cell adhesion molecule-1 (VCAM-1), intercellular adhesion molecule-1 (ICAM-1), and E-selectin. In the earliest stage of the atherosclerotic lesion, there is a localized endothelial expression of VCAM-1 and selective recruitment of mononuclear leukocytes that express the integrin counterreceptor VLA-4. Because of the selective expression of VLA-4 on monocytes and lymphocytes, but not neutrophils, VCAM-1 is important in mediating the selective adhesion of mononuclear leukocytes. Subsequent conversion of leukocytes to foamy macrophages results in the synthesis of a wide variety of inflammatory cytokines, growth factors, and chemoattractants that help propagate the leukocyte and platelet recruitment, smooth muscle cell proliferation, endothelial cell activation, and extracellular matrix synthesis characteristic of maturing atherosclerotic plaque.

VCAM-1 is a mediator of chronic inflammatory disorders such as asthma, rheumatoid arthritis and autoimmune diabetes. For example, it is known that the expression of VCAM-1 and ICAM-1 are increased in asthmatics. Pilewski, J. M., et al. *Am. J Respir. Cell Mol. Biol.* 12, 1–3 (1995); Ohkawara, Y., et al., *Am. J. Respir. Cell Mol. Biol.* 12, 4–12 (1995). Additionally, blocking the integrin receptors for VCAM-1 and ICAM-1 (VLA-4 and LFA-1, respectively) suppressed both early and late phase responses in an ovalbumin-sensitized rat model of allergic airway responses. Rabb, H. A., et al., *Am. J. Respir. Care Med.* 149, 1186–1191 (1994). There is also increased expression of endothelial adhesion molecules, including VCAM-1, in the microvasculature of rheumatoid synovium. Koch, A. E. et al., *Lab. Invest.* 64, 313–322 (1991); Morales-Ducret, J. et al., *Immunol.* 149, 1421–1431 (1992). Neutralizing antibodies directed against VCAM-1 or its counter receptor, VLA-4, can delay the onset of diabetes in a mouse model (NOD mice) which spontaneously develop the disease. Yang, X. D. et al., *Proc. Natl. Acad. Sci. U.S.A.* 90, 10494–10498 (1993); Burkly, L. C. et al., *Diabetes* 43, 523–534 (1994); Baron, J. L. et al., *J. Clin. Invest.* 93, 1700–1708 (1994). Monoclonal antibodies to VCAM-1 can also have a beneficial effect in animal models of allograft rejection, suggesting that inhibitors of VCAM-1 expression may have utility in preventing transplant rejection. Oroez, C. G. et al., *Immunol. Lett.* 32, 7–12 (1992).

VCAM-1 is expressed by cells both as a membrane bound form and as a soluble form. The soluble form of VCAM-1 has been shown to induce chemotaxis of vascular endothelial cells in vitro and stimulate an angiogenic response in rat cornea. Koch, A. F. et al., *Nature* 376, 517–519 (1995). Inhibitors of the expression of soluble VCAM-1 have potential therapeutic value in treating diseases with a strong angiogenic component, including tumor growth and metastasis. Folkman, J., and Shing, Y., *Biol. Chem.* 10931–10934 (1992).

U.S. Pat. Nos. 5,750,351; 5,807,884; 5,811,449; 5,846,959; 5,773,231, and 5,773,209 to Medford, et al., as well as the corresponding WO95/30415 to Emory University indicate that polyunsaturated fatty acids ("PUFAs") and their hydroperoxides ("ox-PUFAs"), which are important components of oxidatively modified low density lipoprotein (LDL), induce the expression of VCAM-1, but not intercellular adhesion molecule-1 (ICAM-1) or E-selectin in human aortic endothelial cells, through a mechanism that is not mediated by cytokines or other noncytokine signals. This is a fundamental discovery of an important and previously unknown biological pathway in VCAM-1 mediated immune responses.

The induction of VCAM-1 by PUFAs and their fatty acid hydroperoxides is suppressed by dithiocarbamate salts, including pyrrolidine dithiocarbamate (PDTC). This indicates that the induction is mediated by an oxidized signal molecule, and that the induction is prevented when the oxidation of the molecule is blocked (i.e., the oxidation does not occur), reversed (i.e., the signal molecule is reduced), or when the redox modified signal is otherwise prevented from interacting with its regulatory target.

Dithiocarbamates

Dithiocarbamates and related compounds have been reviewed extensively by several authors, including G. D. Thorn et al. in a book entitled "The Dithiocarbamates and Related Compounds," Elsevier, New York, 1962. Dithiocarbamates are transition metal chelators clinically used for heavy metal intoxication. Baselt, R. C., F. W. J. Sunderman, et al. (1977), "Comparisons of antidotal efficacy of sodium diethyldithiocarbamate, D-penicillamine and triethylenetetramine upon acute toxicity of nickel carbonyl in rats." *Res Commun Chem Pathol Pharmacol* 18(4): 677–88; Menne, T. and K. Kaaber (1978), "Treatment of pompholyx due to nickel allergy with chelating agents." *Contact Dermatitis* 4(5): 289–90; Sunderman, F. W. (1978), "Clinical response to therapeutic agents in poisoning from mercury vapor" *Ann Clin Lab Sci* 8(4): 259–69; Sunderman, F. W. (1979), "Efficacy of sodium diethyldithiocarbamate (dithiocarb) in acute nickel carbonyl poisoning." *Ann Clin Lab Sci* 9(1): 1–10; Gale, G. R., A. B. Smith, et al. (1981), "Diethyldithiocarbamate in treatment of acute cadmium poisoning." *Ann Clin Lab Sci* 11(6): 476–83; Jones, M. M. and M. G. Cherian (1990), "The search for chelate antagonists for chronic cadmium intoxication." *Toxicology* 62(1): 1–25; Jones, S. G., M. A. Basinger, et al. (1982), "A comparison of diethyldithiocarbamate and EDTA as antidotes for acute cadmium intoxication." *Res Commun Chem Pathol Pharmacol* 38(2): 271–8; Pages, A., J. S. Casas, et al. (1985), "Dithiocarbamates in heavy metal poisoning: complexes of N,N-di (1-hydroxyethyl)dithiocarbamate with Zn(II), Cd(II), Hg(II), CH3Hg(II), and C6H5Hg(II).: *J. Inorg Biochem* 25(1): 35–42; Tandon, S. K., N. S. Hashmi, et al. (1990), "The lead-chelating effects of substituted dithiocarbamates." *Biomed Environ Sci* 3(3): 299–305.

Researchers in oncology have evaluated the use of a number of dithiocarbamates in various cancer-treatment applications. For example, PCT WO 99/01118 of Chinery et al. discloses the use of antioxidants to enhance the treatment of hyperproliferative disorders such as cancer. The publication states that antioxidants can be combined with antineoplastic agents such as 5-fluorouracil (5-FU) to potentiate the activity of the antineoplastic agent to more effectively treat breast cancer, colon cancer, and other cancers. The publication indicates that dithiocarbamates which act as antioxidants are required, and specifically exemplifies dithiocarbamates of the formula, $R_2NC(S)SR$, in which the nitrogen of the dithiocarbamate functionality is a tertiary amine. The nitrogen forms part of a heterocycle, or it is disubstituted by two alkyl groups or variants thereof.

Dithiocarbamates have also been used adjunctively in cis-platinum chemotherapy to prevent renal toxicity. For example, M. Hacker et al. in *Cancer Res* 42(11): 4490–4 (1982), reported on the effect of disulfiram (tetraethylthiuram disulfide) and diethyldithiocarbamate on the bladder toxicity and antitumor activity of cyclophosphamide in mice. See also Borch et al., U.S. Pat. No. 4,594,238 (disclosing the use of dialkyl-dithiocarbamates to reduce the toxicity of antineoplastic platinum compounds); U.S. Pat. No. 5,002,755 to Mitchell et al. (disclosing the use of dethyldithiocarbamate, di(hydroxyethyl)dithiocarbamate, and N-methyl, N-dithiocarboxy-D-glucamine to reduce nephrotoxicity of platinum compounds).

U.S. Pat. No. 5,187,193 to Borch et al. discloses the use of dithiocarbamate salts and acids to treat damaged bone marrow and to stimulate the production of bone marrow cell growth factors. U.S. Pat. No. 5,294,430 to Borch et al. discloses that dithiocarbamates can reverse the damage to the blood-forming function of the bone marrow (myelosuppression) caused by treatment with non-platinum antineoplastic agents. The general disclosure of both patents indicates that the nitrogen function of the dithiocarbamate can be part of a heterocyclic ring, or it can be substituted by two alkyl moieties or by one alkyl moiety and one hydrogen. Exemplary dithiocarbamates include diethyldithiocarbamate, N-methyl-glucamine dithiocarbamate and pentamethylene dithiocarbamate.

The CAS abstract for Japanese Kokai 55-015457 (CAS Abstract No. 1981:139788) discloses compounds having the formula $RR^1(CH_2)_mNHC(S)SCH_2CHR^2COR^3$, wherein: R and $R^1$ can be methyl, ethyl, or together can form a phenyl ring; $R^2$ is H or methyl; and $R^3$ is a saturated heterocyclic ring bound to the compound through nitrogen. The abstract indicates that these compounds have anti-inflammatory, anti-rheumatic, hypotensive, immunosuppressant, and anti-cancer activities.

The CAS abstract for Japanese Kokai 51-105016 (CAS Abstract No. 1977:30075) discloses compounds of the general formula $(aralkyl)-NHC(S)SCH_2CH(NH_2)CO_2R$, wherein R is H, alkyl, alkenyl, alkynyl, cycloalkyl, or lower haloalkyl. The abstract indicates that these compounds display antibacterial, anticarcinogenic, and herbicidal activity.

The CAS abstract for Japanese Kokai 49-135942 (CAS Abstract No. 1975:156722) discloses symmetric compounds of the general formula $ROOCCH(NH_2)CH_2SC(S)NHCH_2$-phenyl-$CH_2NHC(S)SCH_2CH(NH_2)COOR$, and indicates that these compounds can be used as antimicrobial drugs and anticancer drugs.

The CAS abstract for French patent publication 2596987 (CAS Abstract No. 1988:548872) indicates that compounds of the formula NH2NHCSNHNH2 proved active against leukemia in a murine model, and also displayed antibacterial effects against *Escherichia coli, Staphylococcus aureus*, and tuberculosis in vitro.

Research into inflammation and cardiovascular disease has also focused on dithiocarbamates. For example, U.S. Pat. Nos. 5,380,747; 5,792,787; 5,783,596; 5,750,351; 5,821,260; 5,807,884; 5,811,449; 5,846,959; 5,877,203; and 5,773,209 to Medford, et al., teach the use of dithiocarbamate salts and acids for the treatment of cardiovascular and other inflammatory diseases. Examples include sodium pyrrolidine-N-carbodithioate, trisodium N,N-di (carboxymethyl)-N-carbodithioate, and sodium N,N-diethyl-N-carbodithioate. The dithiocarbamates disclosed in these patents all are disubstituted at the nitrogen of the dithiocarbamate function by alkyl or variant thereof, or the nitrogen is part of a heterocyclic ring. As mentioned above, the CAS abstracts for Japanese Kokais 55-015457, 51-105016, and 49-135942, and the CAS abstract for French patent publication 2425431, disclose various compounds characterized by the intermediate dithiocarbamate moiety —NHC(S)S—, and disclose various inflammatory indications for such compounds.

In addition, the CAS abstract for Japanese Kokai 54-141726 (CAS Abstract No. 1980:181659) discloses N-substituted dithiocarbamates of the general formula NR2-alkylene-NHC(S)S-alkylene-CH(NHR)COOR (wherein R2 is H, alkyl, or forms a heterocycle with N), and indicates that the compounds inhibit leukocytopenia and act as adjuvants in the treatment of arthritis.

The CAS abstract for Japanese Kokai 48-005771 (CAS Abstract No. 1976:446399) discloses an N-substituted dithiocarbamate ester of the formula (isopropyl)-NHC(S)S-CH2-(pyridine)-CH2O2NHR, and indicates that the compound was hypotensive in spontaneously hypertensive rats.

U.S. Pat. Nos. 4,173,644, 4,120,972, and 4,120,966 to Brown et al. disclose 2-(5-methyl-4-imidazolylmethylthio) ethyl N-methyldithiocarbamate, and indicate that the compound can act as a histamine $H_2$-antagonist, and is thus useful as an anti-inflammatory agents and as an inhibitor on the effects of histamine on blood pressure.

PCT WO 00/00192 filed by Boyle at el. discloses cyclic dithiocarbamates, of the formula $R^1R^2NC(S)SR$, wherein $R^1$ and $R^2$ constitute a heterocycle that includes the nitrogen of the dithiocarbamate moiety. The reference indicates that the compounds are useful to ameliorate or prevent inflammation.

U.S. Pat. No. 4,166,866 to Wight et al. disclose the use of thioesters of dithiocarbanilic acid or corresponding aryl-substituted dithiocarbanilic acids as immunosuppressants.

U.S. Pat. No. 3,875,170 to Matsumoto et al. disclose the use of pyridine bis(dithiocarbamate) derivatives as anti-hypertensive and anti-inflammatory agents.

U.S. Pat. No. 4,202,832 discloses thiocarbamoylthio fatty acids of the formula aryl-alkylene-NHC(S)S-alkylene-X, wherein X is an acid, ester, amide, or cyano, and indicates that the compounds are useful lipid lowering agents.

U.S. Pat. No. 5,563,159 to Kusaba et al. discloses dithiocarbinimide derivatives of dithiocarbamate esters useful as agaricidal, fungicidal and insecticidal agents.

U.S. Pat. No. 5,344,842 to Missbach discloses thiosemi-carbazone derivatives that are useful for treating rheumatoid-type diseases.

It is an object of this invention to provide new methods, compositions, and strategies for treating hyperproliferative disorders, including cancer.

Another object of the present invention is to provide methods of improving the efficacy, and/or reducing the toxicity, of antineoplastic agents administered in the treatment of hyperproliferative disorders.

It is another object to provide new methods and compositions to treat VCAM-1 mediated diseases such as cardiovascular disease and inflammatory disorders.

It is another object to provide new methods of using N-substituted dithiocarbamate esters in the treatment of biological disorders.

It is still another object to provide new classes of N-substituted dithiocarbamate esters, and pharmaceutical formulations from such classes.

SUMMARY OF THE INVENTION

Certain N-substituted dithiocarbamate esters have been identified that have activity against hyperproliferative conditions. These compounds can be used to treat hyperproliferative conditions alone, or can be used in combination with one or more other antineoplastic agents. When used in combination with another antineoplastic agent, the combination can inhibit cellular proliferation to a greater extent than either compound administered individually.

Moreover, the combined dosage of antineoplastic agents with these N-substituted dithiocarbamate esters exhibits a desired degree of selectivity with respect to transformed (for example cancerous) versus non-transformed cell types, indicating that the compounds are more toxic to transformed cells than normal cells. In other words, the non-transformed cell types are less susceptible to the growth-inhibitory effects of a combined treatment than transformed cell types. These discoveries provide a therapeutic basis for the use of these N-substituted dithiocarbamate esters in the treatment of cancer and other diseases characterized by hyperproliferative cell growth.

The N-substituted dithiocarbamate esters of the present invention contain the dithiocarbamate functionality (—$NR_2C(S)S$—), in which one of the R groups is hydrogen. The "N-substituted dithiocarbamate esters," as defined in more detail herein, thus all have a carbamate nitrogen with one hydrogen substituent. It has surprisingly been found that these N-substituted dithiocarbamate esters have independent chemotherapeutic activity even though many of these compounds are not antioxidants. The compounds may also potentiate the activity of antineoplactic agents.

A preferred class of N-substituted dithiocarbamate esters is defined by the following general formula (I):

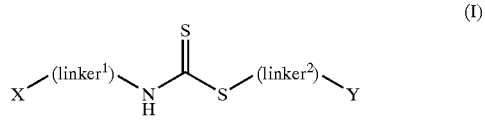

(I)

a) wherein:
b) X is selected from alkyl, alkenyl, alkynyl, heterocyclic, heteroaryl, aryl, aralkyl, heterocyclicalkyl, heteroarylalkyl, alkaryl, alkylheterocyclic, or alkylheteroaryl which can be optionally substituted;
c) Y is selected independently from H, CN, OR, OC(O)R, C(O)NR$^1$R$^2$, C(O)R, NR$^1$R$^2$, C(O)(OR), amino acid, alkyl, alkenyl, alkynyl, heterocyclic, heteroaryl, aryl, aralkyl, heterocyclicalkyl, heteroarylalkyl, alkaryl, alkylheterocyclic, or alkylheteroaryl which can be optionally substituted; and wherein R, R$^1$ and R$^2$ are independently H, alkyl, alkenyl, alkynyl, heterocyclic, heteroaryl, aryl, aralkyl, heterocyclicalkyl, heteroarylalkyl, alkaryl, alkylheterocyclic, or alkylheteroaryl which can be optionally substituted; and
d) linker$^1$ and linker$^2$ are independently alkyl, alkenyl, alkynyl, heterocyclic, heteroaryl, aryl, aralkyl, heterocyclicalkyl, heteroarylalkyl, alkaryl, alkylheterocyclic, or alkylheteroaryl, which can be optionally substituted and wherein linker$^1$ can be a direct bond.

In another embodiment, Y is selected independently from CN, OR, OC(O)R, C(O)NR$^1$R$^2$, C(O)R, NR$^1$R$^2$, and C(O)(OR).

Another example of compounds is defined by the following structure (II):

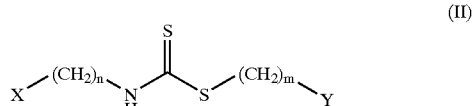

(II)

wherein:
X is a heterocycle or heteroaryl moiety; Y is CN, OR, OC(O)R, C(O)NR$^1$R$^2$, C(O)R, NR$^1$R$^2$, or C(O)(OR); n is 1, 2, 3, or 4 and m is 1, 2, 3, 4, 5, or 6.

The invention thus provides:
1. Defined N-substituted dithiocarbamate esters, and pharmaceutical formulations of such N-substituted dithiocarbamate esters;

2. The use of defined N-substituted dithiocarbamate esters in the treatment of cellular hyperproliferation;
3. The use of N-substituted dithiocarbamate esters in combination with antineoplastic agents in the treatment of cellular hyperproliferation; and
4. The use of N-substituted dithiocarbamate esters to potentiate the efficacy of antineoplastic agents.

It has also been discovered that the defined N-substituted dithiocarbamate esters inhibit the expression of VCAM-1, and thus can be used to treat disorders mediated by VCAM-1. Inflammatory disorders that are mediated by VCAM-1, and which can be treated using the N-substituted dithiocarbamate esters of the present invention, include rheumatoid arthritis, osteoarthritis, asthma, dermatitis, psoriasis, cystic fibrosis, and multiple sclerosis. Cardiovascular disorders that are mediated by VCAM-1, and which can thus be treated using the N-substituted dithiocarbamate esters of the present invention, include atherosclerosis, post-angioplasty restenosis, coronary artery diseases, angina, and small artery disease.

Thus, in still further embodiments the invention provides:
1. Pharmaceutical compositions that comprise a VCAM-1 inhibiting amount of an N-substituted dithiocarbamate ester of the present invention, or its pharmaceutically acceptable salt;
2. Methods for treating diseases or disorders mediated by VCAM-1 by administering an effective amount of a N-substituted dithiocarbamate ester of the present invention.
3. Methods for treating cardiovascular and inflammatory disorders by administering an effective amount of a N-substituted dithiocarbamate ester of the present invention.

In yet another embodiment, certain of these N-substituted dithiocarbamate esters act as inducers of a phase II enzyme, for example, including glutathione S-transferase, UDP-glucuronosyltransferase, and/or quinone oxidoreductase I (NQ01). This can be confirmed using the method described in De Long et al., Proc. Natl Acad Sci USA 83(3):787–791 (1986) and Talalay, Adv. Enzyme Regul. 28:237–250 (1989); Prochaska et al., Cancer Res. 48(17):4776–4782 (1988).

BRIEF DESCRIPTION OF THE FIGURES

FIG. 2 is a schematic depiction of the protocol for performing the Leucomethylene Blue (LMB) assay, an assay which measures the ability to reduce lipid hydroperoxides to the alcohol form.

FIG. 3 is a bar graph showing the results of testing a control, DMSO, PTDC, and 4-(tetrahydrofuran-2-ylmethylthiocarbamoylsulfanyl)-butyric acid methyl ester at concentrations of 25 and 125 $\mu$M, in the LMB assay.

FIG. 4 is an OxyBlot oxidized protein analysis of PTDC and 4-(tetrahydrofuran-2-ylmethylthiocarbamoylsulfanyl)-butyric acid methyl ester showing that PTDC but not 4-(tetrahydrofuran-2-ylmethylthiocarbamoylsulfanyl)-butyric acid methyl ester inhibit cytokine induced oxidatively modified proteins in NHBE cells.

DETAILED DESCRIPTION OF THE INVENTION

Active Compounds

Figure 1:
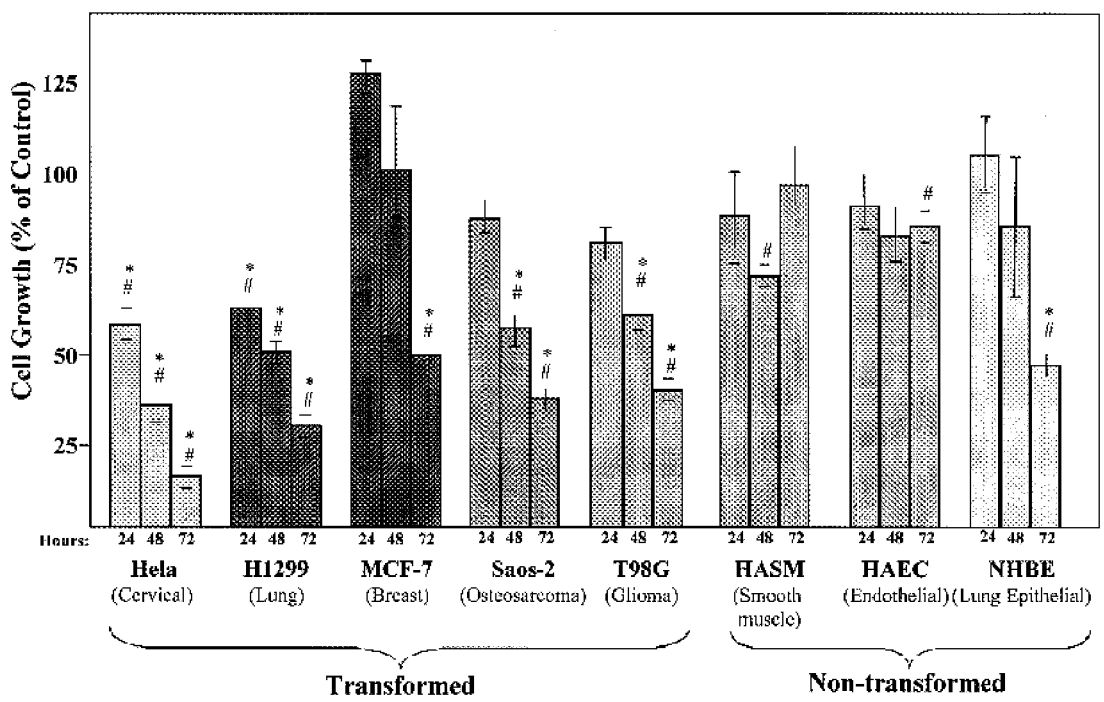
FIG. 1 is a bar graph illustrating the effect of N-substituted dithiocarbamate esters in solid tumor cell lines and three non-transformed cell types. As shown in the figure, there is a time-dependent inhibition of proliferation in all of the transformed cell lines (HeLa, H1299, MCF-7, Saos-2, and T98G) at 10 $\mu$M dithiocarbamate in combination with 0.1 $\mu$M 5-fluorouracil (a concentration of 5-FU in which there was no significant inhibition of proliferation of any cell types when tested alone). In all transformed cell types, by 72 hours the value is significantly different (p<0.05) when compared to both control (DMSO) treated-cells and compared to cultures treated with 0.1 $\mu$M 5-FU alone.

A preferred class of N-substituted dithiocarbamate esters is defined by the following general formula (I):

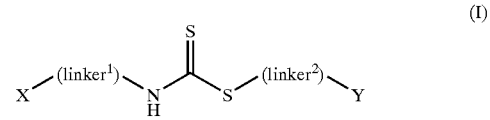

(I)

wherein:
X is selected from alkyl, alkenyl, alkynyl, heterocyclic, heteroaryl, aryl, aralkyl, heterocyclicalkyl, heteroarylalkyl, alkaryl, alkylheterocyclic, or alkylheteroaryl which can be optionally substituted;
Y is selected independently from H, CN, OR, OC(O)R, C(O)NR$^1$R$^2$, C(O)R, NR$^1$R$^2$, C(O)(OR), amino acid, alkyl, alkenyl, alkynyl, heterocyclic, heteroaryl, aryl, aralkyl, heterocyclicalkyl, heteroarylalkyl, alkaryl, alkylheterocyclic, or alkylheteroaryl which can be optionally substituted; and wherein R, R$^1$ and R$^2$ are independently H, alkyl, alkenyl, alkynyl, heterocyclic, heteroaryl, aryl, aralkyl, heterocyclicalkyl, heteroarylalkyl, alkaryl, alkylheterocyclic, or alkylheteroaryl which can be optionally substituted; and
linker$^1$ and linker$^2$ are independently alkyl, alkenyl, alkynyl, heterocyclic, heteroaryl, aryl, aralkyl, heterocyclicalkyl, heteroarylalkyl, alkaryl, alkylheterocyclic, or alkylheteroaryl, which can be optionally substituted and wherein linker$^1$ can be a direct bond.

In another embodiment, Y is selected independently from CN, OR, OC(O)R, C(O)NR$^1$R$^2$, C(O)R, NR$^1$R$^2$, and C(O)(OR).

Another example of compounds is defined by the following structure (II):

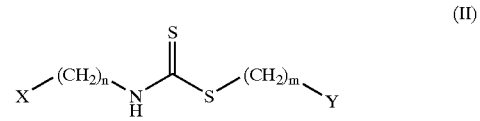

(II)

wherein:
X is a heterocycle or heteroaromatic moiety; Y is CN, OR, OC(O)R, C(O)NR$^1$R$^2$, C(O)R, NR$^1$R$^2$, or C(O)(OR); n is 1, 2, 3, or 4 and m is 1, 2, 3, 4, 5, or 6.

Another class of N-substituted dithiocarbamates is defined by the following structure (II):

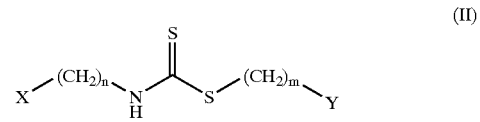

(II)

wherein:
a) X is tetrahydrofuran;
b) Y is independently H, CN or a substituted or unsubstituted group selected from alkyl, alkenyl, alkynyl, OR, OC(O)R, C(O)NR$^1$R$^2$, C(O)R, NR$^1$R$^2$, heterocyclic, heteroaryl, aryl, aralkyl, heterocyclylalkyl, heteroarylalkyl, alkaryl, alkylheterocyclic, or alkylheteroaryl;
c) R, R$^1$ and R$^2$ are H or optionally substituted lower alkyl; and
d) n is 0–12 and m is 1–12.

In another embodiment, the invention provides compounds of formula (I) or (II) wherein:
a) X is an optionally substituted 5 or 6 membered heterocyclic ring;
b) Y is H or a substituted or unsubstituted group selected from alkyl, alkenyl, alkynyl, OR, CN, OC(O)R, C(O)NR$^1$R$^2$, C(O)R, NR$^1$R$^2$, heterocyclic, heteroaryl, aryl, aralkyl, heterocycle-alkyl, heteroarylalkyl, alkaryl, alkylheterocyclic, or alkylheteroaryl;
c) R is H or substituted or unsubstituted lower alkyl;
e) R$^1$ and R$^2$ are independently H, substituted or unsubstituted alkyl, or together with N constitute a 3, 4, 5, 6, or 7 membered heterocyclic or heteroaromatic bridge, such as —(CH$_2$)$_m$— wherein m is 2, 3, 4, 5, or 6;
d) n is 1–3; and
e) m is 1–12.

In another embodiment the invention provides compounds of formula (I) or (II) wherein:
a) X is a substituted or unsubstituted 5 or 6 membered heterocyclic;
b) Y is COOR;
c) n is 1–3; and
d) m is 1–10, preferably 1–5.

In another embodiment the invention provides compounds of formula (I) or (II) wherein:
a) X is a substituted or unsubstituted 5 or 6 membered heterocyclic;
b) Y is OC(OR);
c) n is 1–3; and
d) m is 1–10, preferably 1–5.

In another embodiment the invention provides compounds of formula (I) or (II) wherein:
a) X is a substituted or unsubstituted 5 or 6 membered heterocyclic;
b) Y is C(O)NR$^1$R$^2$;
f) R$^1$ and R$^2$ are independently H, substituted or unsubstituted alkyl, or together with N constitute a 3, 4, 5, 6, or 7 membered heterocyclic or heteroaromatic bridge, such as —(CH$_2$)$_m$— wherein m is 2, 3, 4, 5, or 6;
c) n is 1–3; and
d) m is 1–10, preferably 1–5.

In another embodiment the invention provides compounds of formula (I) or (II) wherein:
a) X is a substituted or unsubstituted 5 or 6 membered heterocyclic;
b) Y is C(O)OR;
c) R is H or lower alkyl;
d) n is 1–3; and
e) m is 1–10, preferably 1–5.

In another embodiment the invention provides compounds of formula (I) or (II) wherein:
a) X is a substituted or unsubstituted 5 or 6 membered heterocyclic;
b) Y is C(O)R;
c) R is lower alkyl, preferably methyl;
d) n is 1–3; and
e) m is 1–10.

In another embodiment the invention provides compounds of formula (I) or (II) wherein:
a) X is an optionally substituted 5 or 6 membered heterocyclic;
b) Y is an optionally substituted aryl, heteroaryl, or heterocyclic;
c) n is 1–3; and
d) m is 1–5.

In still another embodiment the invention provides compounds of formula (I) or (II) wherein:
a) X is an optionally substituted 5 or 6 membered heterocyclic;
b) Y is CN, H, NR$^1$R$^2$, or C(O)(NR$^1$R$^2$), C(O)OR, or OC(OR);
c) R is H or substituted or unsubstituted lower alkyl;
d) R$^1$ and R$^2$ are independently H, substituted or unsubstituted alkyl, or together with N constitute a 3, 4, 5, 6, or 7 membered heterocyclic or heteroaromatic bridge, such as —(CH$_2$)$_m$— wherein m is 2, 3, 4, 5, or 6;
e) n is 1–3; and
f) m is 1–5.

In another embodiment, the invention provides compounds of formula (I) or (II) wherein:
a) X is substituted or unsubstituted aryl or heteroaryl;
b) Y is H, CN or a substituted or unsubstituted group selected from alkyl, alkenyl, alkynyl, OR, OC(O)R, C(O)NR$^1$R$^2$, C(O)R, NR$^1$R$^2$, heterocyclic, heteroaryl, aryl, aralkyl, heterocyclylalkyl, heteroarylalkyl, alkaryl, alkylheterocyclic, or alkylheteroaryl;
c) R is H or substituted or unsubstituted lower alkyl;
g) R$^1$ and R$^2$ are independently H, substituted or unsubstituted alkyl, or together with N constitute a 3, 4, 5, 6, or 7 membered heterocyclic or heteroaromatic bridge, such as —(CH$_2$)$_m$— wherein m is 2, 3, 4, 5, or 6;
d) n is 0–3; and
e) m is 1–10.

In another embodiment the invention provides compounds of formula (I) or (II) wherein:
a) X is optionally substituted aryl or heteroaryl;
b) Y is C(O)OR;
c) R is H or lower alkyl;
d) n is 0–3; and
e) m is 1–10, preferably 1–5.

In another embodiment the invention provides compounds of formula (I) or (II) wherein:
a) X is substituted or unsubstituted aryl or heteroaryl;
b) Y is COOCH$_3$;
c) n is 0–3; and
d) m is 1–10, preferably 1–5.

In another embodiment the invention provides compounds of formula (I) or (II) wherein:
a) X is substituted or unsubstituted aryl or heteroaryl;
b) Y is C(O)NR$^1$R$^2$;
c) R$^1$ and R$^2$ are independently H, substituted or unsubstituted alkyl, or together with N constitute a 3, 4, 5, 6, or 7 membered heterocyclic or heteroaromatic bridge, such as —(CH$_2$)$_m$— wherein m is 2, 3, 4, 5, or 6;
d) n is 0–3; and
e) m is 1–10, preferably 1–5.

In another embodiment the invention provides compounds of formula (I) or (II) wherein:
a) X is substituted or unsubstituted aryl or heteroaryl;
b) Y is C(O)R;
c) R is lower alkyl;
d) n is 0–3; and
e) m is 1–10.

In another embodiment the invention provides compounds of formula (I) or (II) wherein:
a) X is substituted or unsubstituted aryl or heteroaryl;
b) Y is substituted or unsubstituted aryl, heteroaryl, or heterocyclic;
c) n is 0–3; and
d) m is 1–5.

In still another embodiment the invention provides compounds of formula (I) or (II) wherein:
a) X is substituted or unsubstituted aryl or heteroaryl;
b) Y is CN, H, $NR^1R^2$, or $CH(NR^1R^2)C(O)OR$;
c) R is H or substituted or unsubstituted lower alkyl;
d) $R^1$ and $R^2$ are independently H, substituted or unsubstituted alkyl, or together with N constitute a 3, 4, 5, 6, or 7 membered heterocyclic or heteroaromatic bridge, such as —$(CH_2)_m$— wherein m is 2, 3, 4, 5, or 6;
e) n is 0–3; and
f) m is 1–5.

In another embodiment, the invention provides compounds of formula (I) or (II) wherein:
a) X is a substituted or unsubstituted (preferably unsubstituted) 2- or 3-benzofuran, benzothiophene, or indole;
b) Y is H, CN or a substituted or unsubstituted group selected from alkyl, alkenyl, alkynyl, OR, OC(O)R, $C(O)NR^1R^2$, C(O)R, $NR^1R^2$, heterocyclic, heteroaryl, aryl, aralkyl, heterocycyclic-alkyl, heteroarylalkyl, alkaryl, alkylheterocyclic, or alkylheteroaryl;
c) R is H or substituted or unsubstituted lower alkyl;
d) $R^1$ and $R^2$ are independently H or substituted or unsubstituted lower alkyl;
e) n is 1–3; and
f) m is 1–12.

In another embodiment the invention provides compounds of formula (I) or (II) wherein:
a) X is a substituted or unsubstituted (preferably unsubstituted) 2- or 3-benzofuran, benzothiophene, or indole;
b) Y is C(O)OR;
c) R is H or lower alkyl;
d) n is 1–3; and
e) m is 1–10, preferably 1–5.

In another embodiment the invention provides compounds of formula (I) or (II) wherein:
a) X is a substituted or unsubstituted (preferably unsubstituted) 2- or 3-benzofuran, benzothiophene, or indole;
b) Y is C(O)R;
c) R is lower alkyl;
d) n is 1–3; and
e) m is 1–10.

In another embodiment the invention provides compounds of formula (I) or (II) wherein:
a) X is a substituted or unsubstituted (preferably unsubstituted) 2- or 3-benzofuran, benzothiophene, or indole;
b) Y is substituted or unsubstituted aryl, heteroaryl, or heterocyclic;
c) n is 1–3; and
d) m is 1–5.

In still another embodiment the invention provides compounds of formula (I) or (II) wherein:
a) X is an alkyl group;
b) Y is H, CN or a substituted or unsubstituted group selected from alkyl, alkenyl, alkynyl, OR, OC(O)R, $C(O)NR^1R^2$, C(O)R, $NR^1R^2$, heterocyclic, heteroaryl, aryl, aralkyl, heterocyclylalkyl, heteroarylalkyl, alkaryl, alkylheterocyclic, or alkylheteroaryl;
c) R is H or substituted or unsubstituted lower alkyl;
d) $R^1$ and $R^2$ are independently H, substituted or unsubstituted alkyl, or together with N constitute a 3, 4, 5, 6, or 7 membered heterocyclic or heteroaromatic bridge, such as —$(CH_2)_m$— wherein m is 2, 3, 4, 5, or 6;
e) n is 0–3; and
f) m is 1–10.

In another embodiment the invention provides compounds of formula (I) or (II) wherein:
a) X is a substituted or unsubstituted carbohydrate;
b) Y is C(O)OR;
c) R is H or lower alkyl;
d) n is 0–3; and
e) m is 1–10.

In another embodiment the invention provides compounds of formula (I) or (II) wherein:
a) X is a substituted or unsubstituted carbohydrate;
b) Y is an amino acid;
c) n is 0–3; and
d) m is 1–10.

In another embodiment the invention provides compounds of formula (I) or (II) wherein:
a) X is a substituted or unsubstituted carbohydrate;
b) Y is $C(O)NR^1R^2$;
c) $R^1$ and $R^2$ are independently is H or lower alkyl;
d) n is 0–3; and
e) m is 1–10.

In another embodiment the invention provides compounds of formula (I) or (II) wherein:
a) X is a substituted or unsubstituted carbohydrate;
b) Y is C(O)R;
c) R is lower alkyl;
d) n is 0–3; and
e) m is 1–10.

In another embodiment the invention provides compounds of formula (I) or (II) wherein:
a) X is a substituted or unsubstituted carbohydrate;
b) Y is substituted or unsubstituted aryl, heteroaryl, or heterocyclic;
c) n is 0–3; and
d) m is 1–5.

In another embodiment the invention provides compounds of formula (I) or (II) wherein:
a) X is a substituted or unsubstituted carbohydrate;
b) Y is CN, H, $NR^1R^2$, or $CH(NR^1R^2)C(O)OR$;
c) R is H or substituted or unsubstituted lower alkyl;
d) $R^1$ and $R^2$ are independently H, substituted or unsubstituted alkyl, or together with N constitute a 3, 4, 5, 6, or 7 membered heterocyclic or heteroaromatic bridge, such as —$(CH_2)_m$— wherein m is 2, 3, 4, 5, or 6;
e) n is 0–3; and
f) m is 1–5.

In another embodiment the invention provides compounds of formula (I) or (II) wherein:
a) X is substituted or unsubstituted heterocyclic, heteroaryl, heteroarylalkyl or heterocyclicalkyl, wherein the heterocyclic or heteroaryl binds to the molecule through a carbon in the ring of the heterocyclic or heteroaryl;
b) Y is H, CN or a substituted or unsubstituted group selected from alkyl, alkenyl, alkynyl, OR, OC(O)R, C(O)$NR^1R^2$, C(O)R, $NR^1R^2$, carbohydrate, amino acid, heterocyclic, heteroaryl, aryl, aralkyl, heterocyclicalkyl, heteroarylalkyl, alkaryl, alkylheterocyclic, or alkylheteroaryl;
c) R is H or substituted or unsubstituted lower alkyl;
d) $R^1$ and $R^2$ are independently H, substituted or unsubstituted alkyl, or together with N constitute a 3, 4, 5, 6, or 7 membered heterocyclic or heteroaromatic bridge, such as —$(CH_2)_m$— wherein m is 2, 3, 4, 5, or 6;
e) n is 0–3; and
f) m is 1–10.

In another embodiment the invention provides compounds of formula (I) or (II) wherein:
a) X is substituted or unsubstituted heterocyclic, heteroaryl, heteroarylalkyl or heterocyclicalkyl, wherein the heterocyclic or heteroaryl binds to the molecule through a carbon in the ring of the heterocyclic or heteroaryl;
b) Y is C(O)OR;
c) R is H or lower alkyl;
d) n is 0–3; and
e) m is 1–10.

In another embodiment the invention provides compounds of formula (I) or (II) wherein:
a) X is substituted or unsubstituted heterocyclic, heteroaryl, heteroarylalkyl or heterocyclicalkyl, wherein the heterocyclic or heteroaryl binds to the molecule through a carbon in the ring of the heterocyclic or heteroaryl;
b) Y is an amino acid;
c) n is 0–3; and
d) m is 1–10.

In another embodiment the invention provides compounds of formula (I) or (II) wherein:
a) X is substituted or unsubstituted heterocyclic, heteroaryl, heteroarylalkyl or heterocyclicalkyl, wherein the heterocyclic or heteroaryl binds to the molecule through a carbon in the ring of the heterocyclic or heteroaryl;
b) Y is C(O)$NR^1R^2$;
c) $R^1$ and $R^2$ are independently is H or lower alkyl;
d) n is 0–3; and
e) m is 1–10.

In another embodiment the invention provides compounds of formula (I) or (II) wherein:
a) X is substituted or unsubstituted heterocyclic, heteroaryl, heteroarylalkyl or heterocyclicalkyl, wherein the heterocyclic or heteroaryl binds to the molecule through a carbon in the ring of the heterocyclic or heteroaryl;
b) Y is C(O)R;
c) R is lower alkyl;
d) n is 0–3; and
e) m is 1–10.

In another embodiment the invention provides compounds of formula (I) or (II) wherein:
a) X is substituted or unsubstituted heterocyclic, heteroaryl, heteroarylalkyl or heterocyclicalkyl, wherein the heterocyclic or heteroaryl binds to the molecule through a carbon in the ring of the heterocyclic or heteroaryl;
b) Y is substituted or unsubstituted aryl, heteroaryl, or heterocyclic;
c) n is 0–3; and
d) m is 1–5.

In another embodiment the invention provides compounds of formula (I) or (II) wherein:
a) X is substituted or unsubstituted heterocyclic, heteroaryl, heteroarylalkyl or heterocyclic-alky;
b) Y is CN, H, $NR^1R^2$, or CH($NR^1R^2$)C(O)OR;
c) R is H or substituted or unsubstituted lower alkyl;
d) $R^1$ and $R^2$ are independently H, substituted or unsubstituted alkyl, or together with N constitute a 3, 4, 5, 6, or 7 membered heterocyclic or heteroaromatic bridge, such as —$(CH_2)_m$— wherein m is 2, 3, 4, 5, or 6;
e) n is 0–3; and
f) m is 1–5.

The following rules are nonlimiting embodiments of the selection of variables within the foregoing embodiments and subembodiments, and the construction and elucidation of subembodiments. These are not meant to limit the invention.

When X or Y is a substituted hydrocarbon, any substituent can be on the hydrocarbon that does not adversely affect the desired properties of the molecule. Examples are hydroxyl, carboxy, carboalkoxy, amido, acyl, amino, alkylamino, arylamino, alkoxy, aryloxy, nitro, cyano, halo, sulfonic acid, sulfate, phophonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference. The substitution is for example hydroxy, amino ($NR^1R^2$ wherein $R^1$ and $R^2$ are independently hydrogen or lower alkyl), lower alkoxy, cyano, or halo. If X or Y is a substituted or unsubstituted aryl moiety, heteroaryl, or heterocyclic, the substitution can be for example halo, lower alkoxy (for example methoxy), or lower alkyl (for example methyl).

If Y is OC(O)R or COR, then R is preferably lower alkyl (for example methyl, ethyl, or butyl), and m is preferably 1–5.

If X is a substituted or unsubstituted aryl, heteroaryl, or heterocyclic, then such aryl, heteroaryl, or heterocyclic is in one embodiment monocyclic.

If X is a five membered heterocyclic or heteroaryl, then in one embodiment it is linked to the molecule at the 2 or 3 position, but preferably linked at the 2 position. If Y is a six membered heterocyclic or heteroaryl, then in another embodiment it is linked at the 2, 3, or 4 position to the molecule, but it is preferably linked at the 2 or 3 position.

If X or Y comprises an amino or amide moiety ($NR^1R^2$ or C(O)$NR^1R^2$), then $R^1$ and $R^2$ preferably independently comprise H or methyl or ethyl.

In any of the foregoing embodiments, m and n are in one embodiment 1–5. This is especially true whenever X and/or Y are aryl, heteroaryl, or heterocycle. Moreover, in any of the foregoing embodiments in which X or Y is arylalkyl, heteroarylalkyl, or heterocyclic-alkyl, it will be understood that preferred alkyl moieties are lower alkyl.

Some of the foregoing compounds are identified in the examples hereto. Other examples of compounds are listed in Tables I and II below, where the variables are defined for formulas (II) and (III), respectively.

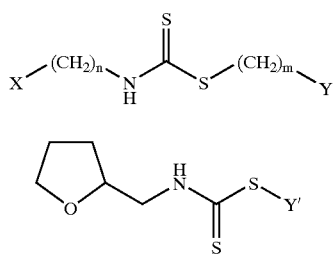

(II)

(III)

TABLE I

| X | Y' | N | m |
|---|----|---|---|
| (tetrahydrofuran-3-yl) | C(O)OCH$_3$ | 1 | 3 |
| (furan-3-yl) | C(O)OCH$_3$ | 1 | 3 |
| (2,3-dihydrobenzofuran-2-yl) | C(O)OCH$_3$ | 1 | 3 |
| (benzofuran-2-yl) | C(O)OCH$_3$ | 1 | 3 |
| (2,3-dihydrobenzofuran-3-yl) | C(O)OCH$_3$ | 1 | 3 |
| (benzofuran-3-yl) | C(O)OCH$_3$ | 1 | 3 |
| (2,3-dihydroxy-tetrahydrofuran-thio derivative) | C(O)OCH$_3$ | 1 | 3 |

TABLE I-continued

| X | Y' | N | m |
|---|----|---|---|
| (3,4-dihydroxy-tetrahydrofuran-2-ylmethyl) | C(O)OCH$_3$ | 1 | 3 |
| (3,4-dihydroxy-tetrahydrothiophen-2-ylmethyl) | C(O)OCH$_3$ | 1 | 3 |
| (tetrahydropyran-2-yl) | C(O)OCH$_3$ | 1 | 3 |
| (1-methylpyrrolidin-2-yl) | C(O)OCH$_3$ | 1 | 3 |
| (pyrrol-2-yl) | C(O)OCH$_3$ | 1 | 3 |
| (pyrrol-3-yl) | C(O)OCH$_3$ | 1 | 3 |
| (5-oxopyrrolidin-2-yl) | C(O)OCH$_3$ | 1 | 3 |
| (1-methyl-5-oxopyrrolidin-2-yl) | C(O)OCH$_3$ | 1 | 3 |
| (pyridin-2-yl) | C(O)OCH$_3$ | 1 | 3 |
| (1-methylpiperidin-2-yl) | C(O)OCH$_3$ | 1 | 3 |
| (pyrazin-2-yl) | C(O)OCH$_3$ | 1 | 3 |

TABLE I-continued
| X | Y' | N | m |
|---|---|---|---|
| pyrimidin-2-yl | C(O)OCH₃ | 1 | 3 |
| thiophen-2-yl | C(O)OCH₃ | 1 | 3 |
| thiophen-3-yl | C(O)OCH₃ | 1 | 3 |
| tetrahydrothiophen-2-yl | C(O)OCH₃ | 1 | 3 |
| benzothiophen-2-yl | C(O)OCH₃ | 1 | 3 |
| benzothiophen-3-yl | C(O)OCH₃ | 1 | 3 |
TABLE II
Y'
CH₂CH(NH₂)C(O)OH
(CH₂)₂CH(NH₂)C(O)OH
(CH₂)₃C(O)NH₂
(CH₂)₃C(O)N(CH₃)₂
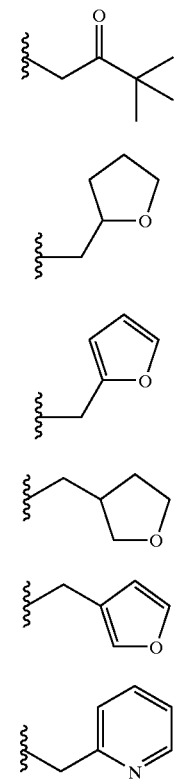

TABLE II-continued

Y'

[structure: pyridin-3-ylmethyl group]

Nonlimiting examples of compounds according to this invention are provided below.

(Tetrahydrofuran-2-ylmethyl)dithiocarbamic acid methyl ester;
(Tetrahydrofuran-2-ylmethylthiocarbamoylsulfanyl)acetic acid methyl ester;
3-(Tetrahydrofuran-2-ylmethylthiocarbamoylsulfanyl)-propionic acid methyl ester;
4-(Tetrahydrofuran-2-ylmethylthiocarbamoylsulfanyl)-butyric acid methyl ester;
6-(Tetrahydrofuran-2-ylmethylthiocarbamoyl-sulfanyl) hexanoic acid methyl ester;
4-(Tetrahydrofuran-2-ylmethylthiocarbamoylsulfanyl)-butyric acid;
(Tetrahydrofuran-2-ylmethyl)dithiocarbamic acid 4-oxo-pentyl ester;
(Tetrahydrofuran-2-ylmethyl)dithiocarbamic acid 3-cyano-propyl ester;
2-Amino-3-(tetrahydrofuran-2-ylmethylthiocarbamoyl-sulfanyl)propionic acid;
2-Amino-4-(tetrahydrofuran-2-ylmethylthiocarbamoyl-sulfanyl)butyric acid;
(Tetrahydrofuran-2-ylmethyl)dithiocarbamic acid 3-carbamoyl-propyl ester;
(Tetrahydrofuran-2-ylmethyl)dithiocarbamic acid 3-dimethylcarbamoyl-propyl ester;
(Tetrahydrofuran-2-ylmethyl)dithiocarbamic acid benzyl ester;
(Tetrahydrofuran-2-ylmethyl)dithiocarbamic acid 2,4-dichloro-benzyl ester;
(Tetrahydrofuran-2-ylmethyl)dithiocarbamic acid phenyl ester;
(Tetrahydrofuran-2-ylmethyl)dithiocarbamic acid 4-chloro-phenyl ester;
(Tetrahydrofuran-2-ylmethyl)dithiocarbamic acid 2,4-difluoro-phenyl ester;
(Tetrahydrofuran-2-ylmethyl)dithiocarbamic acid tetrahydrothiophen-2-ylmethyl ester;
(Tetrahydrofuran-2-ylmethyl)dithiocarbamic acid thiophen-2-ylmethyl ester;
(Tetrahydrofuran-2-ylmethyl)dithiocarbamic acid tetrahydrothiophen-3-ylmethyl ester;
(Tetrahydrofuran-2-ylmethyl)dithiocarbamic acid thiophen-3-ylmethyl ester;
(Tetrahydrofuran-2-ylmethyl)dithiocarbamic acid 2,5-dichloro-thiophen-3-ylmethyl ester;
(Tetrahydrofuran-2-ylmethyl)dithiocarbamic acid 3,3-dimethyl-2-oxo-butyl ester;
(Tetrahydrofuran-2-ylmethyl)dithiocarbamic acid tetrahydrofuran-2-ylmethyl ester;
(Tetrahydrofuran-2-ylmethyl)dithiocarbamic acid furan-2-ylmethyl ester;
(Tetrahydrofuran-2-ylmethyl)dithiocarbamic acid tetrahydrofuran-3-ylmethyl ester;
(Tetrahydrofuran-2-ylmethyl)dithiocarbamic acid furan-3-ylmethyl ester;
(Tetrahydrofuran-2-ylmethyl)dithiocarbamic acid pyridin-2-ylmethyl ester;
(Tetrahydrofuran-2-ylmethyl)dithiocarbamic acid pyridin-3-ylmethyl ester;
4-((S)-Tetrahydrofuran-2-ylmethylthiocarbamoyl-sulfanyl) butyric acid methyl ester;
4-((R)-Tetrahydrofuran-2-ylmethylthiocarbamoyl-sulfanyl) butyric acid methyl ester;
3-(Furan-2-ylmethylthiocarbamoyl-sulfanyl)propionic acid methyl ester;
3-(Methylthiocarbamoylsulfanyl)propionic acid methyl ester;
3-(Ethoxycarbonylthiocarbamoylsulfanyl)propionic acid methyl ester;
4-(2-Methoxy-ethylthiocarbamoylsulfanyl)butyric acid methyl ester;
4-(Tetrahydrofuran-2-ylmethylsulfanylthio-carbonylamino)butyric acid ethyl ester;
4-(Cyclohexylmethylthiocarbamoylsulfanyl)butyric acid methyl ester;
4-(Benzylthiocarbamoylsulfanyl)butyric acid methyl ester;
Methyldithiocarbamic acid methyl ester;
(5-Chloro-2-methyl-phenyl)dithiocarbamic acid ethyl ester;
4-[2-(1H-Indol-2-yl)ethylthiocarbamoyl-sulfanyl]butyric acid methyl ester;
(2-Amino-3-benzylthiocarbamoylsulfanyl)propionic acid;
(3-Methoxybenzyl)dithiocarbamic acid 3,3-dimethyl-2-oxo-butyl ester;
(Pyridin-3-ylmethyl)dithiocarbamic acid 2,5-dichloro-thiophen-3-ylmethyl ester;
Allyldithiocarbamic acid 2-aminoethyl ester hydrochloride;
(2,4-dichlorobenzyl)dithiocarbamic acid 2,4-dichlorobenzyl ester;
Phenethyldithiocarbamic acid dodecyl ester;
(3-Methoxypropyl)dithiocarbamic acid 4-chlorophenyl ester;
Methyldithiocarbamic acid 2,4-difluorophenyl ester;
3-(5-Chloro-2-methylphenylthiocarbamoyl-sulfanyl) propionic acid methyl ester;
3-(2-Diethylamino-ethylthiocarbamoylsulfanyl)-propionic acid methyl ester;
4-(Allylthiocarbamoylsulfanyl)butyric acid methyl ester;
4-[2-(1-Methylpyrrolidin-2-yl)ethylthiocarbamoyl-sulfanyl] butyric acid methyl ester;
Isobutyldithiocarbamic acid 2,4-dichlorobenzyl ester;
4-(Tetrahydrofuran-3-ylmethylthiocarbamoylsulfanyl) butyric acid methyl ester;
4-(Furan-3-ylmethylthiocarbamoylsulfanyl)butyric acid methyl ester;
4-(2,3-Dihydrobenzofuran-2-ylmethylthiocarbamoylsulfanyl)butyric acid methyl ester;
4-(Benzofuran-2-ylmethylthiocarbamoylsulfanyl)-butyric acid methyl ester;
4-(2,3-Dihydrobenzofuran-3-ylmethylthiocarbamoylsulfanyl)butyric acid methyl ester;
4-(Benzofuran-3-ylmethylthiocarbamoylsulfanyl)-butyric acid methyl ester;
4-(3S,4R-Dihydroxytetrahydrofuran-2S-ylmethylthiocarbamoylsulfanyl)butyric acid; methyl ester;
4-(3R,4R-Dihydroxytetrahydrofuran-2R-ylmethylthiocarbamoylsulfanyl)butyric acid; methyl ester;
4-(3R,4R-Dihydroxy-5R methyltetrahydrofuran-2S-ylmethylthiocarbamoylsulfanyl)butyric acid methyl ester;
4-(Tetrahydropyran-2-ylmethylthiocarbamoylsulfanyl) butyric acid methyl ester;
4-(1-Methylpyrrolidin-2-ylmethylthiocarbamoylsulfanyl) butyric acid methyl ester;

4-(1H-Pyrrol-2-ylmethylthiocarbamoylsulfanyl)butyric acid methyl ester;
4-(1H-Pyrrol-3-ylmethylthiocarbamoylsulfanyl)butyric acid methyl ester;
4-(5-Oxo-pyrrolidin-2-ylmethylthiocarbamoylsulfanyl) butyric acid methyl ester;
4-(1-Methyl-5-oxo-pyrrolidin-2-ylmethylthiocarbamoylsulfanyl)butyric acid methyl ester;
4-(Pyridin-2-ylmethylthiocarbamoylsulfanyl)butyric acid methyl ester;
4-(1-Methylpiperidin-2-ylmethylthiocarbamoylsulfanyl) butyric acid methyl ester;
4-(Pyrazin-2-ylmethylthiocarbamoylsulfanyl)butyric acid methyl ester;
4-(Pyrimidin-2-ylmethylthiocarbamoylsulfanyl)butyric acid methyl ester;
4-(Thiophen-2-ylmethylthiocarbamoylsulfanyl)butyric acid methyl ester;
4-(Thiophen-3-ylmethylthiocarbamoylsulfanyl)butyric acid methyl ester;
4-(Tetrahydrothiophen-2-ylmethylthiocarbamoylsulfanyl) butyric acid methyl ester;
4-(Benzo[b]thiophen-2-ylmethylthiocarbamoylsulfanyl) butyric acid methyl ester; and
4-(Benzo[b]thiophen-3-ylmethylthiocarbamoylsulfanyl) butyric acid methyl ester.

The N-substituted dithiocarbamate esters of the present invention preferably display VCAM-1 $IC_{50}$ inhibition concentrations of less than about 25, 15, 10, or 5 µM, or $LD_{50}$ concentrations greater than twice, thrice, five times, or ten times the VCAM-1 $IC_{50}$ concentration.

In still another embodiment the N-substituted dithiocarbamate esters do not exhibit any meaningful antioxidant activity, as measured by the leucomethylene blue assay or the OxyBlot assay (as set forth in more detail in the examples hereto). In a preferred embodiment the N-substituted dithiocarbamate esters display antioxidant activity which is less than one fifth or even one tenth of that displayed by PTDC (pyrrolidine dithiocarbamate) when measured by the leucomethylene blue assay.

Pharmaceutically Acceptable Salts

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

In one particular salt embodiment, it is contemplated that m will be zero and Y will be H, in which case H can be substituted by any pharmaceutically acceptable cation, including but not limited to those cations mentioned in the definitional section hereof.

Stereoisomerism and Polymorphism

It is appreciated that compounds of the present invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms and how to determine antiproliferative activity using the standard tests described herein, or using other similar tests which are well known in the art. Examples of methods that can be used to obtain optical isomers of the compounds of the present invention include the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme iv) enzymatic asymmetric synthesis—a synthetic technique whereby at least one step of the synthesis uses an enzymatic reaction to obtain an enatiomerically pure or enriched synthetic precursor of the desired enantiomer;

v) chemical asymmetric synthesis—a synthetic technique whereby the desired enantiomer is synthesized from an achiral precursor under conditions that produce assymetry (i.e., chirality) in the product, which may be achieved using chrial catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

Definitions

The term alkyl, as used herein, unless otherwise specified, refers to a saturated straight, branched, or cyclic, primary, secondary, or tertiary hydrocarbon, typically of $C_1$ to $C_{18}$, and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of hydroxyl, carboxy, carboxamido, carboalkoxy, acyl, amino, alkylamino, arylamino, alkoxy, aryloxy, nitro, cyano, sulfonic acid, sulfate, phophonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference. Examples of substituted alkyl groups include trifluoromethyl and hydroxymethyl.

The term lower alkyl, as used herein, and unless otherwise specified, refers to a $C_1$ to $C_5$ saturated straight, branched, or if appropriate, a cyclic (for example, cyclopropyl) alkyl group. The lower alkyl group can be optionally substituted in the same manner as described above for the alkyl group.

The term "alkenyl," as referred to herein, and unless otherwise specified, refers to a straight, branched, or cyclic hydrocarbon of $C_2$ to $C_{10}$ with at least one double bond. The alkenyl group can be optionally substituted in the same manner as described above for the alkyl group.

The term "alkynyl," as referred to herein, and unless otherwise specified, refers to a $C_2$ to $C_{10}$ straight or branched hydrocarbon with at least one triple bond. The alkynyl group can be optionally substituted in the same manner as described above for the alkyl group.

The term "—$(CH_2)_n$—" represents a saturated alkylidene radical of straight chain configuration. The term "n" can be any whole integer, including 0, 1, 2, 3, 4, 5, 6, 7, 8, 9, or 10. The moiety "—$(CH_2)_n$—" thus represents a bond (i.e., when n=0), methylene, 1,2-ethanediyl or 1,3-propanediyl, etc.

The term aryl, as used herein, and unless otherwise specified, refers to phenyl, biphenyl, or naphthyl, and preferably phenyl. The aryl group can be optionally substituted with one or more moieties selected from the group consisting of hydroxyl, acyl, amino, halo, carboxy, carboxamido, carboalkoxy, alkylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term heteroaryl or heteroaromatic, as used herein, refers to an aromatic or unsaturated cyclic moiety that includes at least one sulfur, oxygen, nitrogen, or phosphorus in the aromatic ring. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, pyridazinyl, pyrazinyl, cinnolinyl, phthalazinyl, quinoxalinyl, xanthinyl, hypoxanthinyl, and pteridinyl. Functional oxygen and nitrogen groups on the heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acycl groups such as acetyl and propionyl, methanesulfonyl, and p-toluenelsulfonyl. The heteroaryl or heteroaromatic group can be optionally substituted with one or more moieties selected from the group consisting of hydroxyl, acyl, amino, halo, alkylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term heterocyclic refers to a saturated nonaromatic cyclic group which may be substituted, and wherein there is at least one heteroatom, such as oxygen, sulfur, nitrogen, or phosphorus in the ring. The heterocyclic group is preferably linked through a carbon atom to the N-substituted dithiocarbamate. The heterocyclic group can be substituted in the same manner as described above for the heteroaryl group.

The term aralkyl, as used herein, and unless otherwise specified, refers to an aryl group as defined above linked to the molecule through an alkyl group as defined above. The term alkaryl, as used herein, and unless otherwise specified, refers to an alkyl group as defined above linked to the molecule through an aryl group as defined above. The aralkyl or alkaryl group can be optionally substituted with one or more moieties selected from the group consisting of hydroxyl, carboxy, carboxamido, carboalkoxy, acyl, amino, halo, alkylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term halo, as used herein, specifically includes chloro, bromo, iodo, and fluoro.

The term alkoxy, as used herein, and unless otherwise specified, refers to a moiety of the structure —O-alkyl, wherein alkyl is as defined above.

The term acyl, as used herein, refers to a group of the formula C(O)R', wherein R' is an alkyl, aryl, alkaryl or aralkyl group, or substituted alkyl, aryl, aralkyl or alkaryl, wherein these groups are as defined above.

The term "amino acid" includes synthetic and naturally occurring amino acids, including but not limited to, for example, alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl.

The term pharmaceutically acceptable salts or complexes refers to salts or complexes that retain the desired biological activity of the compounds of the present invention and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —NR$^+$A$^-$, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The term carbohydrate generally refers to a compound of carbon, hydrogen, and oxygen that contains the saccharose unit or its first reaction product and in which the ratio of hydrogen to oxygen is the same as in water. The carbohydrates of the present invention can, however, be substituted or deoxygenated at one or more positions, in which case the ratio of hydrogen to oxygen will be different than water. Carbohydrates thus include substituted and unsubstituted monosaccharides, disaccharides, oligosaccharides, and polysaccharides. The saccharide can be an aldose or ketose, and may comprise 3, 4, 5, 6, or 7 carbons, although pyranose and furanose sugars, and acyclic polyol analogs of the formula —CH$_2$—(CHOH)$_{3-4}$CH$_2$OH are preferred. Preferred carbohydrates are monosaccharides.

Non limiting examples of carbohydrates comprising pyranose and furanose sugars include threose, ribulose, ketose, gentiobiose, aldose, aldotetrose, aldopentose, aldohexose, ketohexose, ketotetrose, ketopentose, erythrose, threose, ribose, deoxyribose, arabinose, xylose, lyxose, allose, altrose, glucose, mannose, gulose, idose, glactose, talose, erythrulose, ribulose, xylulose, psicose, fructose, sorbose, tagatose, dextrose, maltose, lactose, sucrose, cellulose, aldose, amylose, palatinose, trehalose, turanose, cellobiose, amylopectin, glucosamine, mannosamine, fucose, phamnose, glucuronate, gluconate, glucono-lactone, muramic acid, abequose, rhamnose, gluconic acid, glucuronic acid, and galactosamine.

The carbohydrate can be optionally deoxygenated at any corresponding C-position, and/or substituted with one or more moieties such as hydrogen, halo, haloalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound. Examples of substituents include amine and halo, particularly fluorine. The substituent or carbohydrate can be either unprotected, or protected as necessary, as known to those skilled in the art, for example, as taught in Greene, et al., *Protective Groups in Organic Synthesis*, John Wiley and Sons, Second Edition, 1991, hereby incorporated by reference. In a preferred embodiment the monosaccharide is a furanose such as (L or D)-ribose.

Exemplary carbohydrates include those presented below in Table III.

TABLE III

Z

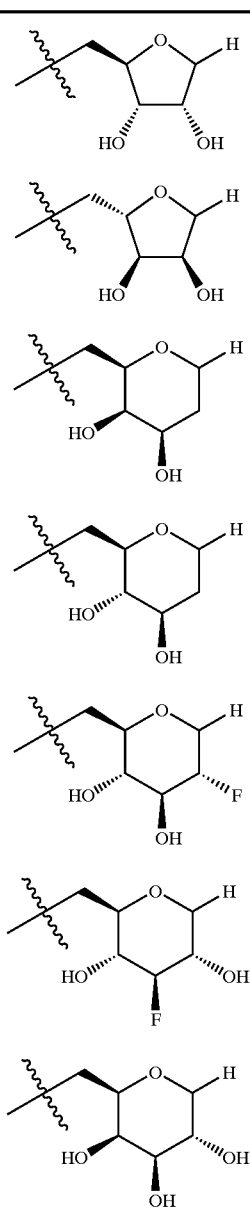

TABLE III-continued

Z

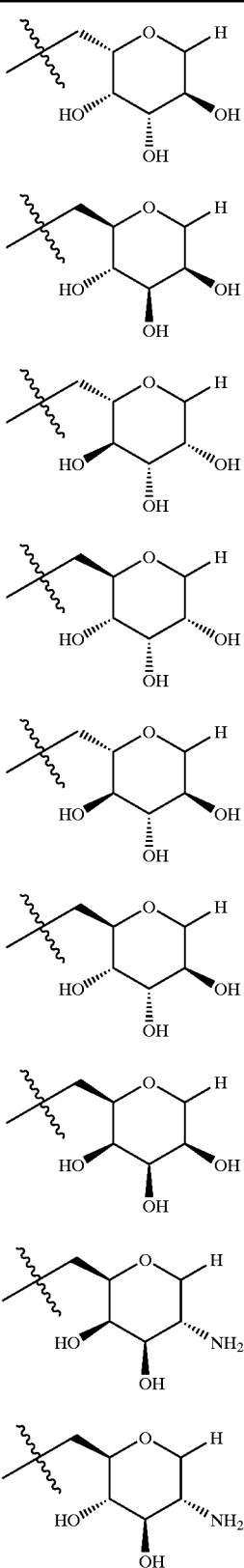

TABLE III-continued

Z

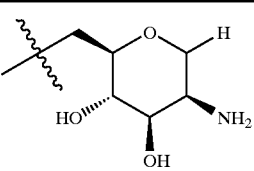

Hyperproliferative Disorders

In one aspect the invention provides a method for treating a proliferative cell disease comprising administering an effective amount of a N-substituted dithiocarbamate ester, or a pharmaceutically acceptable salt thereof.

In a second embodiment, the N-substituted dithiocarbamate ester is administered in combination with another chemotherapeutic agent. As used herein, the term "proliferative cell disease" refers to any cellular disease that is marked by an abnormal rate of cellular mitosis, i.e. a rate of cellular mitosis which is greater than the rate of normally dividing cells, and which can be treated with a chemotherapeutic agent. Such cells are referred to herein as "abnormally proliferative cells." A cell proliferative disease may, for example, be associated with increased transcription and translation of an amplified target DNA sequence. The term "proliferative cell disease" denotes malignant as well as non-malignant cell populations which morphologically often appear to differ from the surrounding tissue.

Malignant cell populations can reside in the various organ systems, such as, for example, lung, breast, lymphoid, hematopoietic, gastrointestinal, and genitourinary tract as well as adenocarcinomas which include malignancies such as most colon cancers, renal-cell carcinoma, prostate cancer, non-small cell carcinoma of the lung, ovarian cancer, brain cancer, uterine cancer, bladder cancer, cancer of the small intestine, and cancer of the esophagus.

Besides cancer, the term "proliferative cell disease" includes non-malignant and immunological-related cell-proliferative diseases such as psoriasis, pemphigus vulgaris, Behcet's syndrome, acute respiratory distress syndrome (ARDS), ischemic heart disease, post-dialysis syndrome, leukemia, rheumatoid arthritis, acquired immune deficiency syndrome, vasculitis, lipid histiocytosis, septic shock and inflammation in general.

Examples of proliferative cell diseases are given in tables IV and V, though by no means are these listings intended to be exhaustive.

TABLE IV

Examples of non-malignant proliferative disorders treatable with N-substituted dithiocarbamate esters

| Organ System | Disease/Pathology |
|---|---|
| Dermatological | Psoriasis (all forms), acne vulgaris, acne rosacea, common warts, anogenital (venereal) warts, eczema; lupus associated skin lesions; dermatitides such as seborrheic dermatitis and solar dermatitis; keratoses such as seborrheic keratosis, senile keratosis, actinic keratosis, photo-induced keratosis, skin ageing, including photo-induced skin aging, keratosis follicularis; keloids and Prophylaxis against keloid formation; leukoplakia, lichen planus, keratitis, contact dermatitis, eczema, |

TABLE IV-continued

Examples of non-malignant proliferative disorders treatable with N-substituted dithiocarbamate esters

| Organ System | Disease/Pathology |
|---|---|
| | urticaria, pruritus, hidradenitis, acne inversa. |
| Cardiovascular | Hypertension, vasculo-occlusive diseases including Atherosclerosis, thrombosis and restenosis after angioplasty; acute coronary syndromes such as unstable angina, myocardial infarction, ischemic and non-ischemic cardiomyopathies, post-MI cardiomyopathy and myocardial fibrosis, substance-induced cardiomyopathy. |
| Endocrine | Insulin resistant states including obesity, diabetes mellitus (types 1 & 2), diabetic retinopathy, macular degeneration associated with diabetes, gestational diabetes, impaired glucose tolerance, polycystic ovarian syndrome; osteoporosis, osteopenia, accelerated aging of tissues and organs including Werner's syndrome. |
| Urogenital | Endometriosis, benign prostatic hyperplasia, leiomyoma, Polycystic kidney disease, diabetic nephropathy. |
| Pulmonary | Asthma, chronic obstructive pulmonary disease (COPD), reactive Airway disease, pulmonary fibrosis, pulmonary hypertension. |
| Connective tissue/joints | Immunological/Rheumatoid arthritis, Raynaud's phenomenon/disease, Sjogren's Syndrome systemic sclerosis, systemic lupus erythematosus, vasculitides, ankylosing spondylitis, osteoarthritis, reactive arthritis, psoriatic arthritis, fibromyalgia. |
| Other | Fibrocystic breast disease, fibroadenoma, chronic fatigue syndrome. |

TABLE V

Examples of neoplastic diseases or malignancies diseases treatable with N-substituted dithiocarbamate esters

| Organ System | Malignancy/Cancer type |
|---|---|
| Skin | Basal cell carcinoma, melanoma, squamous cell carcinoma; cutaneous T cell lymphoma; Kaposi's sarcoma. |
| Hematological | Acute leukemia, chronic leukemia and myelodysplastic syndromes. |
| Urogenital | Prostatic, renal and bladder carcinomas, anogenital carcinomas including cervical, ovarian, uterine, vulvar, vaginal, and Those associated with human papilloma virus infection. |
| Neurological | Gliomas including glioblastomas, astrocytoma, ependymoma, medulloblastoma, oligodendroma; meningioma, pituitary adenoma, neuroblastoma, craniopharyngioma. |
| Gastrointestinal | Colon, colorectal, gastric, esophageal, mucocutaneous carcinomas. |
| Breast | Breast cancer including estrogen receptor and progesterone Receptor positive or negative subtypes, soft tissue tumors. |
| Metastasis | Metastases resulting from the neoplasms. |
| Other | Angiomata, angiogenesis associated with the neoplasms. |

Chemotherapeutic Agent

As used herein, a "chemotherapeutic agent" is a type of antiproliferative agent, and particularly is a compound that has biological activity against one or more forms of cancer. Suitable chemotherapeutic agents include antineoplasts. Representative antineoplasts include adjuncts, androgen inhibitors, antibiotic derivatives, antiestrogens, antimetabolites, cytotoxic agents, hormones, immunomodulators, nitrogen mustard derivatives and steroids. Physicians' Desk Reference, 50th Edition, 1996.

Representative adjuncts include levamisole, gallium nitrate, granisetron, sargramostim strontium-89 chloride, filgrastim, pilocarpine, dexrazoxane, and ondansetron. Physicians' Desk Reference, 50th Edition, 1996.

Representative androgen inhibitors include flutamide and leuprolide acetate. Physicians' Desk Reference, 50th Edition, 1996.

Representative antibiotic derivatives include doxorubicin, bleomycin sulfate, daunorubicin, dactinomycin, and idarubicin.

Representative antiestrogens include tamoxifen citrate and analogs thereof. Physicians' Desk Reference, 50th Edition, 1996. Additional antiestrogens include nonsteroidal antiestrogens such as toremifene, droloxifene and roloxifene. Magarian et al., Current Medicinal Chemistry, 1994, Vol. 1, No. 1.

Representative antimetabolites include fluorouracil, fludarabine phosphate, floxuridine, interferon alfa-2b recombinant, methotrexate sodium, plicamycin, mercaptopurine, and thioguanine. Physicians' Desk Reference, 50th Edition, 1996.

Representative cytotoxic agents include doxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplati, cisplati, cisplatin, interferon alfa-2a recombinant, paclitaxel, teniposide, and streptozoci. Physicians' Desk Reference, 50th Edition, 1996.

Representative hormones include medroxyprogesterone acetate, estradiol, megestrol acetate, octreotide acetate, diethylstilbestrol diphosphate, testolactone, and goserelin acetate. Physicians' Desk Reference, 50th Edition, 1996.

Representative immunodilators include aldesleukin. Physicians' Desk Reference, 50th Edition, 1996.

Representative nitrogen mustard derivatives include melphalan, chlorambucil, mechlorethamine, and thiotepa. Physicians' Desk Reference, 50th Edition, 1996.

Representative steroids include betamethasone sodium phosphate and betamethasone acetate. Physicians' Desk Reference, 50th Edition, 1996.

Specifically, the chemotherapeutic agent can be an antineoplastic agent.

Specifically, the antineoplastic agent can be a cytotoxic agent.

Specifically, the cytotoxic agent can be 5-FU, FdUMP, cisplatin, etoposide, adriamycin, or 5-aza-2'-deoxycytidine.

Additional suitable chemotherapeutic agents include alkylating agents, antimitotic agents, plant alkaloids, biologicals, topoisomerase I inhibitors, topoisomerase II inhibitors, and synthetics. AntiCancer Agents by Mechanism, ttp://www.dtp.nci.nih.gov/docs/cancer/searches/standard_mechanism_list.html, Apr. 12, 1999; Approved Anti-Cancer Agents, http://www.ctep.info.nih.gov/handbook/HandBookText/fda_agen.htm, pages 1–7, Jun. 18, 1999; MCMP 611 Chemotherapeutic Drugs to Know, http//www.vet.purdue.edu/ depts/bms/ courses/mcmp611/chrx/drg2no61.html, Jun. 24,1999; and *Chemotherapy,* http://www. vetmed.1su.edu/oncology/ Chemotherapy.htm, Apr. 12, 1999.

Representative alkylating agents include asaley, AZQ, BCNU, busulfan, bisulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864. *AntiCancer Agents by Mechanism,* http://dtp.nci.nih.gov/docs/cancer/searches/standard_mechanism_list.html, Apr. 12, 1999.

Representative antimitotic agents include allocolchicine, Halichondrin B, colchicine, colchicine derivatives, dolastatin 10, maytansine, rhizoxin, paclitaxel derivatives, paclitaxel, thiocolchicine, trityl cysteine, vinblastine sulfate, and vincristine sulfate. *AntiCancer Agents by Mechanism,* http://dtp.nci.nih.gov/docs/cancer/searches/standard_mechanism_list.html, Apr. 12, 1999.

Representative plant alkaloids include actinomycin D, bleomycin, L-asparaginase, idarubicin, vinblastine sulfate, vincristine sulfate, mitramycin, mitomycin, daunorubicin, VP-16-213, VM-26, navelbine and taxotere. *Approved Anti-Cancer Agents,* http://ctep.info.nih.gov/handbook/HandBookText/fda_agent.htm, Jun. 18, 1999.

Representative biologicals include alpha interferon, BCG, G-CSF, GM-CSF, and interleukin-2. *Approved Anti-Cancer Agents,* http://ctep.info. nih.gov/handbook/HandBookText/fda_agent.htm, Jun. 18, 1999.

Representative topoisomerase I inhibitors include camptothecin, camptothecin derivatives, and morpholino-doxorubicin. *AntiCancer Agents by Mechanism,* http://dtp.nci.nih. gov/docs/cancer/searches/standard_mechanism_list.html, Apr. 12, 1999.

Representative topoisomerase II inhibitors include mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16. AntiCancer Agents by Mechanism, http://dtp.nci.nih.gov/docs/cancer/searches/standard_mechanism_list.html, Apr. 12, 1999.

Representative synthetics include hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium. *Approved Anti-Cancer Agents,* http://ctep. info.nih.gov/handbook/HandBookText/fda_agen.htm, Jun. 18, 1999.

Antiproliferative Agents other than Chemotherapeutic Agents

As discussed above, there are a number of proliferative cell diseases other than cancer that can be treated using the compounds and methods of this invention. Representative agents for treating those non-cancerous proliferative cell diseases are as follows:

Psoriasis: Topical treatments for psoriasis include: Corticosteroids (cortisone); Calcipotriene (a synthetic form of vitamin $D_3$); Coal tar; Anthralin; Topical retinoids (e.g. tazarotene, or Tazorac). Systemic treatments for psoriasis include: Methotrexate; Cyclosporine (Neoral®); Hydroxyurea (Hydrea®); Retinoids such as acitretin (Soriatane®); and Antibiotics.

Rheumatoid arthritis: First line agents for treating rheumatoid arthritis include aspirin and NSAIDS (non-steroidal anti-inflammatory drugs, including Examples of NSAIDS include diclofenac, indomethacin, ketorolac, ketoprofen, naproxen, diflunisal, mefenamic acid, ioxoprofen, tolmefenamic acid, indoprofen, pirprofen, fenoprofen, zaltoprofen, sulindac, tolmetin, suprofen, flurbiprofen, pranoprofen, niflumic acid, flufenamic acid, zomopirac, bromfenac, fenclofenac, alcofenac, orpanoxin, etodolic acid, fleclozic acid, amfenac, emfenamic acid, benoxaprofen, fluoxaprofen, carprofen, isofezolac, aceloferac, fenpufen, fenclorac, meclofenamate, and clindac). Second line agents include gold salts, penicillamine, methotrexate, and antimalarials.

Examples of compounds for treating hyproliferative disorders, when the compound is not administered as a potentiating agent, include compounds defined by formulas (I) and (II) above when X is:

a) a substituted or unsubstituted 5 or 6 membered heteroaryl or heterocyclic;

b) a substituted or unsubstituted 2- or 3-benzofuran, benzothiophene, or indole;

c) a substituted or unsubstituted carbohydrate; or d) substituted or unsubstituted heterocyclic, heteroaryl, heteroarylalkyl or heterocyclicalkyl, wherein the heterocyclic or heteroaryl binds to the molecule through a carbon in the ring of the heterocyclic or heteroaryl.

VCAM-1 Mediated Disease

In another aspect the invention provides a method for treating a disease or disorder mediated by VCAM-1 comprising administering to a patient a VCAM-1 inhibiting effective amount of a N-substituted dithiocarbamate ester of the present invention, or a pharmaceutically acceptable salt thereof. Exemplary effective amounts and modes of administration are set below in "Pharmaceutical Compositions and Modes of Administration." The compound can be administered alone or in combination with other active compounds.

Nonlimiting examples of noncardiovascular inflammatory diseases or disorders that are mediated by VCAM-1 and which can be treated by administering the compounds of the present invention include rheumatoid and osteoarthritis, asthma, dermatitis, psoriasis, cystic fibrosis, post transplantation acute and chronic solid organ rejection, and multiple sclerosis. Nonlimiting examples of cardiovascular diseases or disorders that can be treated by mediating VCAM-1 expression and which can be treated by administering the compounds of the present invention include atherosclerosis, post-angioplasty restenosis, coronary artery disease, angina, and small artery disease.

Examples of compounds for treating VCAM-1 mediated conditions include the compounds of formula II wherein:

X is an optionally substituted 2- or 3-benzofuran, benzothiophene, or indole;

X is an optionally substituted carbohydrate; or

X is an optionally substituted heterocyclic, heteroaryl, heteroarylalkyl or heterocyclicalkyl.

EXAMPLES

The following examples are understood to be illustrative only and are not intended to limit the scope of the present invention in any way.

Example 1

Effect of N-substituted Dithiocarbamate Esters with and without 5-fluorouracil on the Growth of Transformed and Nontransformed Cells The following example was undertaken to determine the effect of N-substituted dithiocarbamate esters with and without 5-fluorouracil on the growth of a variety of transformed and non-transformed cells. Information concerning the cell lines used in this example are given in Table 1.

TABLE 1

Cell Lines

| CELL LINES | CANCER |
|---|---|
| MCF-7 | Breast |
| HeLa | Cervical |
| H1299 | Lung |
| Saos-2 | Osteosarcoma |
| T98G | Brain Glioma |
| DLD-1 | Colorectal |
| Snu-C5 | Colorectal |

| CELL TYPE | NON-TRANSFORMED |
|---|---|
| HASM | Human Aortic Smooth Muscle |
| HAEC | Human Aortic Endothelial Cell |
| NHBE | Normal Human Bronchial Epithelial |

Materials & Methods
Cell Culture

All primary cells and cell lines were commercially available. The transformed cell lines were grown in Dulbecco's Modified Eagle Media supplemented with 2 mM L-glutamine, 50 I.U. penicillin, 50 μg/ml streptomycin, nonessential amino acids and 10% heat-inactivated fetal bovine serum. HASM, HAEC and NHBE cells were cultured exactly as described by the commercial provider (Clonetics, San Diego, Calif.). All cell lines were grown at 37° C. in 5% $CO_2$, with the media being changed every 48 hours.
Cell Plating For the experimental assays, cells were plated in 96-well plates and grown until ~35% confluency was achieved. For the transformed cell lines, cells were plated at low density and grown for 72 hours prior to being stimulated, whereas the non-transformed cells were plated at a higher density and grown for 24 hours prior to being stimulated.
Experimental Protocol Cells were treated with dithiocarbamate (0.1–100 μM)±5FU (0.01–10 μM) and retreated after 48 hours when media was changed. Cell growth was assessed using the CellTiter96® assay system from Promega (Madison, Wis.). Each experimental condition was performed in triplicate or quadruplicate, with the number of experiments for each cell line being three.
Statistical Analysis Statistical significance was assessed using an ANOVA with the appropriate post-hoc analysis as well as Students t-tests. *=p<0.05 when compared to control-treated (DMSO) cells. #=p<0.05 when compared to 5FU-treated cells.
Dithiocarbamate The dithiocarbamate tested in this examples is 4-(tetrahydrofuran-2-ylmethylthiocarbamoylsulfanyl)-butyric acid methyl ester, which is referred to below as NDE.
Results/Discussion The data in tables 2 & 3 demonstrate in two colorectal cell lines (SNU-C5 and DLD-1) a dose- and time-dependent inhibition of proliferation when cells are treated with dithiocarbamate. This inhibition is potentiated at the lower doses of dithiocarbamate (NDE) when combined with a low dose of 5-FU. Similar results were obtained with the colorectal cell line DLD-1 (table 3).

The effect of dithiocarbamate in additional solid tumor cell lines and three non-transformed cell types was determined. As shown in FIG. 1 there is a time-dependent inhibition of proliferation in all of the transformed cell lines (HeLa, H1299, MCF-7, Saos-2, and T98G) at 10 μM dithiocarbamate in combination with 0.1 μM 5-fluorouracil. At this concentration of 5-FU, there was no significant inhibition of proliferation of any cell types when tested alone. In all transformed cell types, by 72 hours the value is significantly different (p<0.05) when compared to both control (DMSO) treated-cells and compared to cultures treated with 0.1 μM 5-FU alone. In some cell types statistical significance is also observed at the 24 and 48 hour time point.

In the non-transformed cell types HASM and HAEC, a time-dependent inhibition of proliferation was not observed. The NHBE cells appeared more sensitive to inhibition of proliferation and exhibited a time-dependent inhibition of proliferation. However, the level of inhibition was generally less than that observed with the other transformed cell types excluding MCF-7.

TABLE 2

Anti-proliferative effects of dithiocarbamate (NDE) with and without 5-fluorouracil on proliferation of SNU-C5 colorectal carcinoma cells. Data is represented as percent of control (cells with no drug treatment).

| | 5-FU Alone (1 μM) | NDE | NDE + 5-FU (1 μM) |
|---|---|---|---|
| 5-FU (1 μM) | | | |
| 24 HOURS | 108.9 | | |
| 48 HOURS | 85.5 | | |
| 72 HOURS | 86.1 | | |
| NDE (1 μM) | | | |
| 24 HOURS | | 138.32 ± 24.20 | 118.87 ± 20.60 |
| 48 HOURS | | 105.47 ± 7.42 | 100.65 ± 18.24 |
| 72 HOURS | | 127.13 ± 16.43 | 80.38 ± 10.48 |
| NDE (10 μM) | | | |
| 24 HOURS | | 93.40 ± 15.88 | 99.20 ± 20.83 |
| 48 HOURS | | 70.47 ± 8.42 | 54.57 ± 19.06 |
| 72 HOURS | | 59.23 ± 4.10 | 30.77 ± 3.80 |
| NDE (100 μM) | | | |
| 24 HOURS | | 60.03 ± 10.77 | 50.37 ± 11.64 |
| 48 HOURS | | 26.30 ± 8.64 | 25.90 ± 6.80 |
| 72 HOURS | | 13.57 ± 1.31 | 16.13 ± 3.89 |

* Values indicated are percent of control.

TABLE 3

Anti-proliferative effects of dithiocarbamate with and without 5-fluorouracil on proliferation of DLD-1 colorectal carcinoma cells. Data is represented as percent of control (cells with no drug treatment).

| | 5-FU Alone (1 μM) | NDE | NDE + 5-FU (1 μM) |
|---|---|---|---|
| 5-FU (1 μM) | | | |
| 24 HOURS | 90.8 | | |
| 48 HOURS | 85.8 | | |
| 72 HOURS | 113.2 | | |
| NDE (1 μM) | | | |
| 24 HOURS | | 115.53 ± 3.72 | 88.92 ± 3.72 |
| 48 HOURS | | 107.02 ± 7.55 | 103.60 ± 6.85 |
| 72 HOURS | | 133.47 ± 10.26 | 146.37 ± 9.74 |
| NDE (10 μM) | | | |
| 24 HOURS | | 97.1 ± 1.79 | 82.37 ± 7.59 |
| 48 HOURS | | 104.10 ± 13.31 | 82.73 ± 14.80 |
| 72 HOURS | | 141.90 ± 14.87 | 82.50 ± 11.91 |

TABLE 3-continued

Anti-proliferative effects of dithiocarbamate with and without 5-fluorouracil on proliferation of DLD-1 colorectal carcinoma cells. Data is represented as percent of control (cells with no drug treatment).

| | 5-FU Alone (1 μM) | NDE | NDE + 5-FU (1 μM) |
|---|---|---|---|
| NDE (100 μM) | | | |
| 24 HOURS | | 53.77 ± 5.28 | 51.27 ± 2.63 |
| 48 HOURS | | 39.80 ± 6.27 | 39.90 ± 4.25 |
| 72 HOURS | | 0.27 ± 0.27 | 0 ± 0 |

* Values indicated are percent of control.

Example 2

Effect of N-substituted Dithiocarbamate Esters on VCAM-1 Inhibition

VCAM-1 Assay

The VCAM-1 assay is an enzyme immunoassay to detect tumor necrosis factor alpha (TNF-α) induced Vascular Adhesion Molecule (VCAM-1) expression in endothelial cells.

Methods

Cell Culture

Human endothelial cells (HAEC) were purchased from Clonetics and maintained in EGM media (Clonetics) supplemented with 5% fetal bovine serum (FBS). In a typical experiment, cells were seeded in 96-well plates. The next day cells were stimulated with TNF-α (1 ng/ml) purchased from Boehringer Mannheim in the presence or absence of compounds dissolved in dimethylsulphoxide (DMSO). To establish a dose curve for each compound, four concentrations in 2 fold increments were used. Cells were exposed to TNF-α and compounds for approximately 16 hours. The next day, cells were examined under microscope to score for visual signs of toxicity.

Immunoassay

Media was discarded and the cells were washed once with Hanks buffered saline solution (HBSS)/phosphate buffered solution (PBS) 91:1). Primary mouse monoclonal antibody against VCAM-1 purchased from Southern Biotechnology Associates (0.25 μg/ml in HBSS/PBS+5% FBS) was added and incubated at 37° C. for 30 minutes. Cells were washed with HBSS/PBS three times, and secondary antibody horse radish peroxidase (HRP)-conjugated goat anti-mouse IgG purchased from Southern Biotechnology Associates (1:500 in HBSS/PBS+5% FBS) was added and incubated at 37° C. for 30 minutes. Cells were washed with HBSS/PBS four times and peroxidase substrate 3.3',5,5'-tetramethylbenzidine (TMB) was added and incubated in the dark at room temperature until there was adequate blue color development. The length of incubation time was typically 5–15 minutes. 2 N sulfuric acid was added to stop the color development and the data was collected by reading the absorbance at O.D. 450 nm. The result was expressed as the percentage of control sample (cells stimulated by TNF without any compound). $IC_{50}$ is the concentration of compound required to inhibit 50% of the TNF stimulated signal.

Results

The VCAM-1 $IC_{50}$ of various N-substituted dithiocarbamate esters is shown in Table 4.

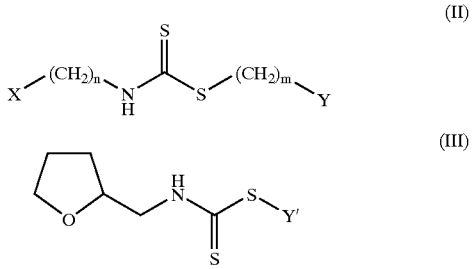

TABLE 4

| X | Y' | N | m | VCAM-1 $IC_{50}$ (μM) | II or III |
|---|---|---|---|---|---|
| (R)-tetrahydrofuran-2-yl | C(O)OCH₃ | 1 | 3 | 3 | II |
| (S)-tetrahydrofuran-2-yl | C(O)OCH₃ | 1 | 3 | 3 | II |
| furan-2-yl | C(O)OCH₃ | 1 | 2 | 6 | II |
| H | C(O)OCH₃ | 1 | 2 | 14 | II |
| ethoxycarbonylmethyl | C(O)OCH₃ | 0 | 2 | 50 | II |
| CH₃O | C(O)OCH₃ | 2 | 3 | 11 | II |
| ethoxycarbonylmethyl | tetrahydrofuran-2-yl | 3 | 1 | 5 | II |
| cyclohexyl | C(O)OCH₃ | 1 | 3 | 40 | II |
| phenyl | C(O)OCH₃ | 1 | 3 | 25 | II |
| H | H | 1 | 1 | NE | II |
| 4-chloro-2-methylphenyl | H | 0 | 2 | NE | II |

TABLE 4-continued

| X | Y' | N | m | VCAM-1 IC$_{50}$ (μM) | II or III |
|---|---|---|---|---|---|
| 1H-indol-2-yl | C(O)OCH$_3$ | 2 | 3 | 5 | II |
| phenyl | CH(NH$_2$)C(O)OH | 1 | 1 | 7 | II |
| 3-methoxyphenyl | C(O)C(CH$_3$)$_3$ | 1 | 1 | 2 | II |
| pyridin-3-yl | 2,5-dichlorothiophen-3-yl | 1 | 1 | 1.5 | II |
| allyl | NH$_2$·HCl | 1 | 2 | 12 | II |
| 2,4-dichlorophenyl | 2,4-dichlorophenyl | 1 | 1 | 8 | II |
| phenyl | H | 2 | 12 | 30 | II |
| 3-methoxyphenyl | 4-chlorophenyl | 3 | 0 | 6 | II |
| H | 2,4-difluorophenyl | 1 | 0 | 18 | II |
| 4-chloro-2-methylphenyl | C(O)OCH$_3$ | 0 | 2 | NE | II |

TABLE 4-continued

| X | Y' | N | m | VCAM-1 IC$_{50}$ (μM) | II or III |
|---|---|---|---|---|---|
| N,N-diethylaminoethyl | C(O)OCH$_3$ | 2 | 3 | 37 | II |
| vinyl | C(O)OCH$_3$ | 1 | 3 | 30 | II |
| 1-methylpyrrolidin-2-yl | C(O)OCH$_3$ | 2 | 3 | 18 | II |
| isobutyl | 2,4-dichlorophenyl | 1 | 1 | 32 | II |
| N/A | CH$_3$ | | | 6.5 | III |
| N/A | CH$_2$C(O)OCH$_3$ | | | 10 | III |
| N/A | (CH$_2$)$_2$C(O)OCH$_3$ | | | 3 | III |
| N/A | (CH$_2$)$_3$C(O)OCH$_3$ | | | 1.5 | III |
| N/A | (CH$_2$)$_5$C(O)OCH$_2$CH$_3$ | | | 11 | III |
| N/A | (CH$_2$)$_3$C(O)OH | | | 7 | III |
| N/A | (CH$_2$)$_3$C(O)CH$_3$ | | | 7 | III |
| N/A | (CH$_2$)$_3$CN | | | 3 | III |

Example 3

Effect of 4-(tetrahydrofuran-2-ylmethylthiocarbamoylsulfanyl)-butyric acid methyl ester on Leucomethylene Blue Leucomethylene Blue Assay The Leucomethylene Blue (LMB) assay measures the ability to reduce lipid hydroperoxides to the alcohol form as depicted in FIG. 2.

Method

Linoleic acid was oxidized by soybean lipoxygenase to generate 13-hydroperoxy-octadecadienoic acid (13-HpODE). In a typical reaction, 2 μl of 50 mM linoleic acid (in alcohol) was mixed with 10 μl of soybean lipoxygenase (100 units) in 988 ml of phosphate buffer saline (PBS). The reaction was monitored for the formation of 13-HpODE by following the diene absorbance at 234 nm, which generally reached a maximum within 45 minutes. Aliqoutes from the lipoxygenase reactions were added to cuvettes containing 500 μl of N-benzoyl leucomethylene blue reagent in the presence or absence of compound. The reagent was prepared by dissolving 5 mg N-benzoyl leucomethylene blue in 8 ml of dimethylforamide (DMF), then adding this solution to a 0.05 M potassium phosphate buffer (pH 5) containing 1.4 g Triton X-100-PC and 5.5 mg hemoglobin and bringing it to a total volume of 100 ml. The solutions in the cuvette were diluted to 750 μl. After 5 minutes at room temperature the UV absorbance of the solution were read at 660 nm.

Results

The results of this assay for a control, dimethylsulfoxide, pyrrolidine dithiocarbamate, and 4-(tetrahydrofuran-2-ylmethylthiocarbamoylsulfanyl)-butyric acid methyl ester are summarized in FIG. 3.

Example 4

OxyBlot Assay of 4-(tetrahydrofuran-2-ylmethylthiocarbamoylsulfanyl)-butyric acid methyl ester OxyBlot™

The OxyBlot™ assay (Intergen) detects oxidative modification of proteins by reactive oxygen species such as hydroxynonenal. As a consequence of the modification, carbonyl groups are introduced into protein side chains by a site-specific mechanism. OxyBlot™ detects these carbonyl groups, which is a hallmark of the oxidation status of proteins.

Methods
Cell Culture

Normal human bronchial epithelial cells (NHBE) were purchased from Clonetics. They were cultured in BEGM (Clonetics) media without retinoic acid. In a typical experiment, the cells were seeded in 24-well plates. Media was changed to BEGM without retinoic acid (RA) and hydrocortisone (HC) 24 hr before dosing. Cells were then exposed to compounds in fresh BEGM without RA and HC for 20 min at 37° C., subsequently stimulated with TNF (10 ng/ml) and IL-4 (20 ng/ml) purchased from Boehringer Mannheim for another 20 min at 37° C. All compounds were dissolved in DMSO and the final concentration of DMSO was 0.2%.

Immunoblot

Cells were washed 3 times with cold PBS, and lysed in 100 μl/well 1×RIPA buffer (25 mM Tris pH7.6, 150 mM NaCl, 2 mM EDTA, 1% IGEPAC, 0.5% deoxycholate, 0.1% SDS), 50 mM DTT, 1 mM PMSF, 10 g/ml leupeptin, 1 μl/ml aprotinin. The cell lysates were clarified by centrifugation. 5 μl of the lysates were mixed with 5 μl 12% SDS (OxyBlot™ kit) and 10 μl of 1×2,4-Dintirophenylhydrazin (DNPH) (OxyBlot™ kit). As negative controls, a parallel set of lysates was mixed with 12% SDS and a 1×Derivatization-Control Solution (OxyBlot™ kit). All samples were then incubated at room temp for 15 min, followed by adding 15 μl of 12% SDS to each sample.

Samples were fractionated by 4–20% gradient SDS-PAGE (NOVEX), transferred onto nitrocellose filters (MSI) and incubated with the filters in Blocking/Dilution Buffer (OxyBlot™ kit) for 1 hour with gentle shaking. Primary antibody (OxyBlot™ kit) was diluted 1:150 in Blocking/Dilution buffer and added to the filters for 1-hour incubation at room temperature. The filters were then washed in 1×PBS-Tween four times. Secondary antibody (OxyBlot™ kit) was diluted 1:300 in Blocking/Dilution Buffer and added to the filters for 1-hour incubation at room temperature. The filters were washed as previous, exposed to chemiluminescence reagents according to the manufacturer's directions and developed by autoradiography film.

Results

The results from the derivatized samples are shown in FIG. 4. The negative control samples did not have any signal on the film.

Example 5

15-Lipoxygenase Form 2 Assay of 4-(tetrahydrofuran-2-ylmethylthiocarbamoylsulfanyl)-butyric acid methyl ester 15-Lipoxygenase Form-2 Assay The 15-Lipoxygenase Form-2 (15-LOX-2) Assay is an immunoblot assay to measure tumor necrosis factor alpha (TNF-α) and interleukin-4 (IL-4) co-induced expression of 15-LOX-2 in Normal Human Epithelial Cells.

Methods
Cell Culture

Normal human bronchial epithelial cells (NHBE) were purchased from Clonetics. They were cultured in BEGM (Clonetics) media without retinoic acid. In a typical experiment, the cells were seeded in 24-well plates. Media was changed to BEGM without retinoic acid (RA) and hydrocortisone (HC) 24 hour before dosing. Cells were then exposed to TNF-α (10 ng/ml) and IL-4 (20 ng/ml) purchased from Boehringer Mannheim in the absence or presence of compounds in fresh BEGM without RA and HC for 16–20 hours at 37° C. To establish a dose curve for each compound, three concentrations in 2 fold increments were used. All compounds were dissolved in DMSO and the final concentration of DMSO was 0.2%.

Immunoblot

Cells were washed with cold 1×PBS three times and then lysed by 100 μl of Tris-Glycine SDS sample buffer (NOVEX). Lysates were fractionated by 4–20% gradient SDS-PAGE (NOVEX), transferred onto nitrocellulose filters (MSI) and incubated with the filters in blocking buffer (5% Blotto in 1×Tris buffered saline (TBS)+0.05% Tween 20) for 1 hour with gentle shaking. Primary antibody (anti-15LOX-2 purchased from Oxford Biomedical) was diluted 1:3000 in blocking buffer and added to the filters for overnight incubation at 4° C. The filters were then washed in 1×TBS-T four times. Secondary antibody (anti-rabbit Ig purchased from Amersham) was diluted 1:5000 in blocking buffer and added to the filters for 1-hour incubation at room temperature. The filters were washed as previous, exposed to chemiluminescence reagents (ECL purchased from Amersham) according to the manufacturer's directions and developed by autoradiography. The images were scanned and analyzed by a software program (NIH Image 1.59) to calculate the $IC_{50}$, which is the concentration of compound required to inhibit 50% of the TNF+IL-4 stimulated signal.

Results

The 15-LOX-2 $IC_{50}$ for 4-(tetrahydrofuran-2-ylmethylthiocarbamoylsulfanyl)-butyric acid methyl ester was 4.5 μM.

Example 6

Eotaxin Assay of 4-(tetrahydrofuran-2-ylmethylthiocarbamoylsulfanyl)-butyric acid methyl ester Eotaxin Assay The eotaxin assay is an enzyme immunoassay to measure tumor necrosis factor alpha (TNF-α) and interleukin-4 (IL-4) induced expression of eotaxin in a human epithelial cell line (BEAS-2B).

Methods
Cell Culture

BEAS-2B cells purchased from ATCC and maintained in DMEM/F12 plus 10% serum and penicillin plus streptomycin. In a typical experiment, cells were seeded in 96-well plates. The next day cells were stimulated with TNF (10 ng/ml)+IL-4 (20 nm/ml) in the presence or absence of compounds dissolved in dimethylsulphoxide (DMSO) in DMEM/F12 plus 1% rabbit serum albumin (RSA). To establish a dose curve for each compound, three concentrations in 2 fold increments were used. Cells were exposed to cytokines and compounds for approximately 16 hours. The next day, the cells were examined under microscope to score for visual signs of toxicity. The culture media was used to measure eotaxin level.

Immunoassay

100 μl of anti-human eotaxin monoclonal antibody (3 μg/ml) purchased from R & D Systems was used to coat 96-well plates overnight at room temperature. The next day the plates were washed with 0.05% Tween 20 in 1×PBS three times and blocked by adding 300 μl of 1×PBS containing 1% BSA, 5% sucrose and 0.05% NaN$_3$ to each well for an hour at room temperature. The plates were washed as previously described. 100 μl of the culture media (no dilution is required) or eotaxin standard (1000, 500, 250, 125, 62.5, 31.25, 15.62, 0 pg/ml in 0.1% BSA, 0.05% Tween 20 in TBS) were added to each well and incubated at room temperature for 2 hr. The plates were washed as previously described. 100 μl of the biotinylated anti-human eotaxin antibody purchased from R & D Systems (150 ng/ml, diluted in 0.1% BSA, 0.05% Tween 20 in TBS) was then added and incubated at room temperature for 2 hr. After another wash, 100 μl of Avid-HRP (1:2000 in 0.1% BSA, 0.05% Tween 20 in TBS) purchased from Boehringer Mannheim was added and incubated at room temperature for 30 min. After the final wash, 100 μl TMB was added. 2N sulphuric acid stopped the color development and data were collected by a microplate reader set at O.D. 450 nm. The results were expressed as the percentage of control sample (cells stimulated by TNF without any compound). IC$_{50}$ is the concentration of compound required to inhibit 50% of the TNF+IL-4 stimulated signal.

Results

The eotaxin IC$_{50}$ of 4-(tetrahydrofuran-2-ylmethylthiocarbamoylsulfanyl)-butyric acid methyl ester was 6 μM.

Example 7

Protocols for Preparation of N-Substituted Dithiocarbamate Esters

The compounds of the present invention can be prepared by utilizing known procedures and techniques, or routine modifications thereof, as generally set forth by Thorn and Ludwig in *The Dithiocarbamates and Related Compounds* (Elsevier Publishing 1962). A general synthetic scheme for preparing the compounds is set forth below.

Protocol A (via Intermediate Dithiocarbamate Salt)

A quantity of amine is dissolved in a suitable solvent (such as THF or DMF or EtOH) and treated with a slight excess (1.1 eq.) of a suitable base (typically NaH or NaOH). The resulting mixture is stirred at room temperature and a slight excess (1.03 eq) of carbon disulfide is added. Stirring of the mixture is continued for at least an additional 2 hours. Solvent is removed by rotary evaporation to give the crude dithiocarbamate salt. The salt is dissolved in a solvent (e.g. DMF or EtOH) suitable for the subsequent alkylation reaction. The solution is stirred and treated with an alkylating reagent (1 eq.) or electrophile (1 eq.). The progress of the reaction is monitored by thin-layer chromatography. The reaction is typically quenched by the addition of an organic solvent (e.g. ethyl acetate) and de-ionized water. The immiscible layers are separated, and the organic layer is dried over anhydrous Na$_2$SO$_4$ or MgSO$_4$. The drying agent is removed by filtration, and the organic phase is then concentrated by rotary evaporation to give the crude dithiocarbamate ester. Purification is accomplished by re-crystallization from a suitable solvent system or by chromatography to give the desired N-substituted dithiocarbamate ester.

Protocol B (via Intermediate Isothiocyanate)

A quantity of thiocarbonyldiimidazole (1.02 eq.) is dissolved in chloroform. De-ionized water is added followed by 0.5 eq. of K$_2$CO$_3$. A quantity of amine (1.0 eq.) in chloroform is added to the mixture. The resulting mixture is stirred. The progress of the reaction is monitored by thin layer chromatography. The immiscible layers are separated, and the organic layer is concentrated by rotary evaporation to give the crude isothiocyanate. The crude isothiocyanate is dissolved in a solvent (e.g. DMF) suitable for the subsequent coupling reaction with a thiol (1 eq.). The progress of the reaction is monitored by thin layer chromatography. A base (e.g. NaH) may be added to accelerate the reaction. The reaction is quenched by partitioning between an organic solvent (e.g. ethyl acetate) and water. The organic phase is separated and dried over anhydrous Na$_2$SO$_4$ or MgSO$_4$. Removal of the drying agent is followed by removal of solvent by rotary evaporation to give the crude dithiocar-

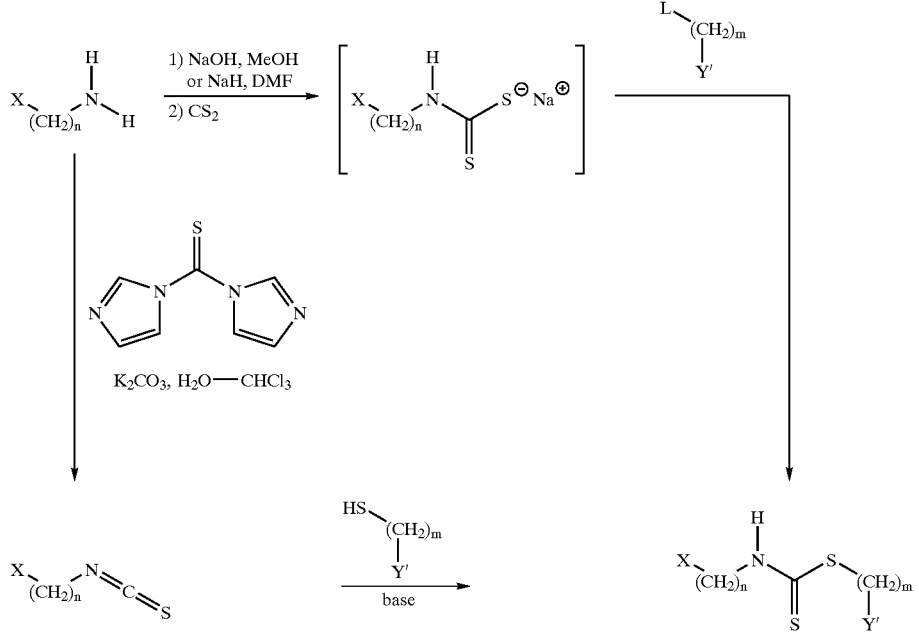

bamate ester. Purification is accomplished by chromatography or by re-crystallization to give the desired N-substituted dithiocarbamate ester.

The compounds in the table below are made according to the synthetic protocols A or B in Example 7.

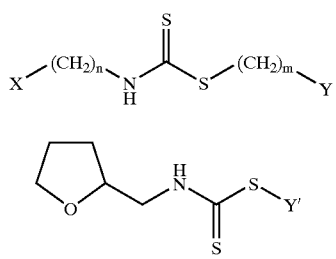

TABLE 4

| X | Y' | N | m | VCAM-1 IC$_{50}$ ($\mu$M) | II or III |
|---|---|---|---|---|---|
| tetrahydrofuran-2-yl (H up) | C(O)OCH$_3$ | 1 | 3 | 3 | II |
| tetrahydrofuran-2-yl (H down) | C(O)OCH$_3$ | 1 | 3 | 3 | II |
| furan-2-yl | C(O)OCH$_3$ | 1 | 2 | 6 | II |
| H | C(O)OCH$_3$ | 1 | 2 | 14 | II |
| ethyl ester | C(O)OCH$_3$ | 0 | 2 | 50 | II |
| CH$_3$O | C(O)OCH$_3$ | 2 | 3 | 11 | II |
| ethyl ester | tetrahydrofuran-2-yl | 3 | 1 | 5 | II |
| cyclohexyl | C(O)OCH$_3$ | 1 | 3 | 40 | II |
| phenyl | C(O)OCH$_3$ | 1 | 3 | 25 | II |
| H | H | 1 | 1 | NE | II |

TABLE 4-continued

| X | Y' | N | m | VCAM-1 IC$_{50}$ ($\mu$M) | II or III |
|---|---|---|---|---|---|
| 5-chloro-2-methylphenyl | H | 0 | 2 | NE | II |
| indol-2-yl | C(O)OCH$_3$ | 2 | 3 | 5 | II |
| phenyl | C(O)CH(NH$_2$)OH | 1 | 1 | 7 | II |
| 3-methoxyphenyl | C(O)C(CH$_3$)$_3$ | 1 | 1 | 2 | II |
| pyridin-3-yl | 2,5-dichlorothiophen-3-yl | 1 | 1 | 1.5 | II |
| allyl | NH$_2$·HCl | 1 | 2 | 12 | II |
| 2,4-dichlorophenyl | 2,4-dichlorophenyl | 1 | 1 | 8 | II |
| phenyl | H | 2 | 12 | 30 | II |
| CH$_3$O | 4-chlorophenyl | 3 | 0 | 6 | II |
| H | 2,4-difluorophenyl | 1 | 0 | 18 | II |

TABLE 4-continued

| X | Y' | N | m | VCAM-1 IC$_{50}$ ($\mu$M) | II or III |
|---|---|---|---|---|---|
| 4-Cl, 2-Me-phenyl | C(O)OCH$_3$ | 0 | 2 | NE | II |
| Et$_2$N-CH$_2$CH$_2$- | C(O)OCH$_3$ | 2 | 3 | 37 | II |
| allyl | C(O)OCH$_3$ | 1 | 3 | 30 | II |
| N-methylpyrrolidin-2-yl | C(O)OCH$_3$ | 2 | 3 | 18 | II |
| isobutyl | 2,4-diCl-phenyl | 1 | 1 | 32 | II |
| N/A | CH$_3$ | | | 6.5 | III |
| N/A | CH$_2$C(O)OCH$_3$ | | | 10 | III |
| N/A | (CH$_2$)$_2$C(O)OCH$_3$ | | | 3 | III |
| N/A | (CH$_2$)$_3$C(O)OCH$_3$ | | | 1.5 | III |
| N/A | (CH$_2$)$_5$C(O)OCH$_2$CH$_3$ | | | 11 | III |
| N/A | (CH$_2$)$_3$C(O)OH | | | 7 | III |
| N/A | (CH$_2$)$_3$C(O)CH$_3$ | | | 7 | III |
| N/A | (CH$_2$)$_3$CN | | | 3 | III |

Example 8

4-(tetrahydrofuran-2-ylmethylthiocarbamoylsulfanyl)-butyric acid methyl ester (NDE)

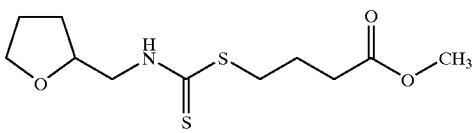

To a solution of tetrahydofurfurylamine (2 mL) in EtOH (20 mL) were added 5 N NaOH (3.9 mL) and carbon disulfide (1.17 mL), and the mixture was stirred for 1.5 h. Methyl 4-chlorobutyrate (2.4 mL) was then added, and the mixture was stirred overnight. Upon quenching with saturated NaCl solution the mixture was extracted with ether. Chromatography on silica gel gave the desired 4-(tetrahydrofuran-2-ylmethylthiocarbamoylsulfanyl)-butyric acid methyl ester product (1.1 g).

Pharmaceutical Compositions and Modes of Administration

Animals, including mammals and specifically humans, suffering from any of the above-described conditions can be treated by the topical, systemic or transdermal administration of a composition comprising an effective amount of a N-substituted dithiocarbamate ester or a pharmaceutically acceptable salt thereof, optionally in a pharmaceutically acceptable carrier or diluent. When treating proliferative cell diseases, the dithiocarbamate can be coadministered with a chemotherapeutic agent, which may also be in the form of a pharmaceutically acceptable salt, and optionally in a pharmaceutically acceptable carrier or diluent.

A proliferative cell disease (such as a tumor) can be located in any part of the mammal. Specifically, the tumor can be located in the breast, lung, thyroid, lymph node, genitourinary system (e.g., kidney, ureter, bladder, ovary, teste, or prostate), musculoskeletal system (e.g., bones, skeletal muscle, or bone marrow), gastrointestinal tract (e.g., stomach, esophagus, small bowel, colon, rectum, pancreas, liver, or smooth muscle), central or peripheral nervous system (e.g., brain, spinal cord, or nerves), head or neck (e.g., ears, eyes, nasopharynx, oropharynx, or salivary glands), or the heart. The mode of administration will depend upon the location and nature of the disease, as known to workers skilled in the art.

The compound of the present invention can be formulated as pharmaceutical compositions and administered to a mammalian host such as a human patient in a variety of forms adapted to the chosen route of administration, i.e., orally or parenterally, by intravenous, intramuscular, or subcutaneous routes. Alternatively, the compound can be administered sublingually, mucosally (e.g. nasally), via inhalation, transdermally, or ophthalmically.

The method herein is also suitably performed through sustained release systems. The sustained release systems can be tailored for administration according to any one of the proposed administration regimes. Slow or extended-release delivery systems, including any of a number of biopolymers (biological-based systems), systems employing liposomes, and polymeric delivery systems, can be utilized with the compositions described herein to provide a continuous or long term source of therapeutic compound(s).

Suitable examples of sustained release compositions include semipermeable polymer matrices in the form of shaped articles, e.g., films, microcapsules, or microspheres. Sustained release matrices include, for example, polylactides (U.S. Pat. No. 3,773,919), copolymers of L-glutamic acid and γ-ethyl-L-glutamate (Sidman et al., Biopolymers 22:547–556, 1983), or poly-D-(–)-3-hydroxybutyric acid (EP 133,988). Sustained release compositions also include one or more liposomally entrapped dithiocarbamates and/or chemotherapeutic agents. Such compositions are prepared by methods known per se, e.g., as taught by Epstein et al. Proc. Natl. Acad. Sci. USA 82:3688–3692, 1985. Ordinarily, the liposomes are of the small (200–800 Å) unilamellar type in which the lipid content is greater than about 30 mol % cholesterol, the selected proportion being adjusted for the optimal therapy.

A variety of techniques to produce microparticles have been described in the prior art. For example, United Kingdom Patent Application No. 2,234,896 to Bodmer et al. describes a method of forming microparticles by mixing a solution of the polymer dissolved in an appropriate solvent with a solution of a drug. Microparticle formation is then induced by the addition of a phase inducing agent. European Patent Application 0 330 180 to Hyon et al. describes a process for preparing polylactic acid-type microparticles by adding a solution of a drug and a polymer in a mixed solvent to a phase inducing agent and evaporating the original solvent microparticle formation. Other examples of processes for preparing microparticles by phase separation technique have been described in U.S. Pat. No. 4,732,763 to Beck et al. and U.S. Pat. No. 4,897,268 to Tice et al. and by Ruiz et al. in the International Journal of Pharmaceutics (1989) 49:69–77 and in Pharmaceutical Research (1990) 9:928–934.

The N-substituted dithiocarbamate esters and/or chemotherapeutics agents may be administered orally in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the substance may be combined with one or more excipients and used in the form of ingestible tablets, buccal tablets, troches, capsules, elixirs, suspensions, syrups, wafers, and the like. Such compositions and preparations should contain at least 0.1% of the substance. The percentage of the compositions and preparations may, of course, be varied and may conveniently be between about 2 to about 60% of the weight of a given unit dosage form. The amount of substance in such therapeutically useful compositions is such that an effective dosage level will be obtained.

Tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the substance may be incorporated into sustained-release preparations and devices.

The N-substituted dithiocarbamate esters and/or chemotherapeutics can also be administered intravenously or intraperitoneally by infusion or injection. Solutions of the substance(s) can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the substance(s) which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, normal saline, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the substance(s) in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Injectable solutions are particularly advantageous for local administration of the therapeutic composition. In particular, intramuscular injection can be used to deliver the dithiocarbamate and chemotherapeutic agent directly to a tumorous growth. Intra-articular injection is a preferred alternative in cases of arthritis where the practitioner wishes to treat one or only a few (such as 2–6) joints. Additionally, the therapeutic compounds are injected directly into lesions (intra-lesion administration) in appropriate cases. Intradermal administration is an alternative for dermal lesions.

The therapeutic compound or compounds are optionally administered topically by the use of a transdermal therapeutic system (see, Barry, Dermatological Formulations, (1983) p. 181 and literature cited therein). While such topical delivery systems have been designed largely for transdermal administration of low molecular weight drugs, by definition they are capable of percutaneous delivery. They can be readily adapted to administration of the therapeutic compounds of the invention by appropriate selection of the rate-controlling microporous membrane. Topical application can also be achieved by applying the compound of interest, in a cream, lotion, ointment, or oil based carrier, directly to the skin. Typically, the concentration of therapeutic compound in a cream, lotion, or oil is 1–2%.

For drug targeting to lung tissue, the therapeutic compound is formulated into a solution, suspension, aerosol or particulate dispersion appropriate for application to the pulmonary system. The therapeutic agent may be inhaled via nebulizer, inhalation capsule, inhalation aerosol, nasal solution, intratracheal as a solution via syringe, or endotracheal tube as an aerosol or via as a nebulizer solution. Aersols are prepared using an aqueous aerosol, liposomal preparation or solid particles containing the compound. A nonaqueous (e.g. fluorocarbon propellant) suspension could be used. Sonic nebulizers are preferred because they minimize exposing the therapeutic compound to shear, which can result in degradation of the compound.

Sublingual tablets are designed to dissolve very rapidly. Examples of such formulations include ergotamine tartrate, isosorbide dinitrate, isoproterenol HCl. The formulation of these tablets contain, in addition to the drug, a limited number of soluble excipients, usually lactose and powdered sucrose, but occasionally dextrose and mannitol. The process of making sublingual tablets involves moistening the blended powder components with an alcohol-water solvent system containing approximately 60% alcohol and 40% water.

In addition to the N-substituted dithiocarbamate ester and/or chemotherapeutic, the prototype formulation for sublingual tablets may contain a binder such as povidone or HPMC, diluents such as lactose, mannitol, starch or cellulose, a disinegrant such as pregelatinized or modified starch, lubricants such as magnesium stearate, stearic acid or hydrogenated vegetable oil, a sweetener such as saccharin or sucrose and suitable flavoring and coloring agents.

Delivery of the N-substituted dithiocarbamate esters and/or chemotherapeutic agents of the instant invention by the mucosal route also offers an attractive administration alternative. The prototype formulation for nasal solutions will contain the compound(s) dissolved in a suitable aqueous or non-aqueous solvent such as propylene glycol, an antioxidant such as ascorbic acid and aromatic oils as flavoring agents. The formulation may also contain suitable propellant (s).

For ophthalmic applications, the N-substituted dithiocarbamate ester and/or chemotherapeutic agent is formulated into solutions, suspensions, and ointments appropriate for use in the eye. For opthalmic formulations, see Mitra (ed.), Ophthalmic Drug Delivery Systems, Marcel Dekker, Inc., New York, N.Y. (1993), and also Havener, W. H., Ocular Pharmacology, C. V. Mosby Co., St. Louis (1983).

Useful dosages of the compounds can be determined by comparing their in vitro activity, and in vivo activity in animal models. Methods for the extrapolation of effective dosages in mice, and other animals, to humans are known to the art; for example, see U.S. Pat. No. 4,938,949. The amount of the substance required for use in treatment will vary not only with the particular salt selected but also with the route of administration, the nature of the condition being treated and the age and condition of the patient and will be ultimately at the discretion of the attendant physician or clinician.

When administered by itself, however, a suitable dose of the N-substituted dithiocarbamate ester will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day. The substance is conveniently administered in unit dosage form; for example, containing 5 to 1000 mg, conveniently 10 to 750 mg, most conveniently, 50 to 500 mg of active ingredient per unit dosage form. Ideally, the N-substituted dithiocarbamate ester should be administered to achieve peak plasma concentrations of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the substance, optionally in saline, or orally administered as a bolus containing about 1–100 mg of the substance. Desirable blood levels may be maintained by continuous infusion to provide about 0.01–5.0 mg/kg/hr or by intermittent infusions containing about 0.4–15 mg/kg of the substance.

When the N-substituted dithiocarbamate ester is coadministered with a chemotherapeutic agent for the treatment of a cellular proliferative disorder, the dosing will generally be based upon the accepted dosing rate and schedule for the chemotherapeutic agent, and the level of N-substituted dithiocarbamate ester which maximally potentiates the efficacy of the chemotherapeutic agent without inducing unacceptable levels of cytotoxicity. However, it should be understood that any concentration of the N-substituted dithiocarbamate ester can be administered to potentiate the activity of the chemotherapeutic agent.

The N-substituted dithiocarbamate ester and/or chemotherapeutic agent may conveniently be presented in a single dose or as divided doses administered at appropriate intervals, for example, as two, three, four or more sub-doses per day.

Biodegradable Implants

In one embodiment the invention provides a biodegradable implant that is inserted into the void created by surgery for removal of a tumor. By the term "biodegradable" is meant capable of being completely removed from the localized area, by physiological metabolic processes. The implant contains the N-substituted dithiocarbamate ester of the present invention and optionally a chemotherapeutic agent, and is present in a sustained release formulation that permits sustained local delivery to the excision site for a substantially predetermined period of time. The implant is useful for any surgery which removes a cancerous tumor from a patient's body, and is particularly useful following the removal of a cancerous growth from the brain, breast, or other bodily tissue.

A number of sustained-release implants are known in the art. Most implants are "matrix" type, and comprise an active compound dispersed in a matrix of a carrier material. The carrier material may be either porous or non-porous, solid or semi-solid, and permeable or impermeable to the active compound. Matrix devices are typically biodegradable, i.e., they slowly erode after administration. Alternatively, matrix devices may be nondegradable, and rely on diffusion of the active compound through the walls or pores of the matrix. Matrix devices are preferred for the applications contemplated herein.

Thus, in one embodiment the invention provides a surgical implant for localized delivery of a chemotherapeutic agent, the N-substituted dithiocarbamate ester of the present invention, and a biodegradable binder. The implant preferably is capable of releasing and delivering the chemotherapeutic agent and dithiocarbamate to substantially all of an area of clear margin that results from a surgical lumpectomy, and is also preferably capable of releasing the compounds at a substantially constant rate for at least one day. In another embodiment the invention provides a method of delivering an N-substituted dithiocarbamate ester and a chemotherapeutic agent to an area of clear margin following a surgical lumpectomy comprising (i) providing an implant comprising the chemotherapeutic agent and dithiocarbamate and a biodegradable binder; and (ii) placing the implant into a void created by the surgical lumpectomy.

The surgical implant can come in a variety of forms. In one embodiment the implant is a bolus, comprising a viscous and deformable material capable of being shaped and sized before implantation to complement a void created by a surgical lumpectomy, and sufficiently deformable upon implantation to contact substantially all of an area of clear margin.

The bolus will typically have a volume of at least about 1 cm$^3$, and is often greater than 5, 10, 20, or 50 cm$^3$ in volume. The implant can also comprise an outer layer and a core, wherein the outer later comprises the dithiocarbamate, and because it contacts the area of clear margin is able to release the active compounds directly to the adjacent tissue in the clear margin.

The surgical implant can also comprising a plurality of capsules that can be poured into the void created by a surgical lumpectomy. These capsules will contain the chemotherapeutic agent, the dithiocarbamate, and a suitable binder. Because they are flowable, they can be poured into the void created by a surgical lumpectomy, and thereby contact substantially all of the area of clear margin.

Many suitable compositions for the implant are known and can be used in practicing the invention. Such compositions are described in, for example, Chasin et. al., Biodegradable Polymers as Drug Delivery Systems, Marcel Dekker Inc., NY, ISBN 0-8247-8344-1, the disclosure of which being incorporated herein by this reference. Preferable compositions are pharmaceutically acceptable, biodegradable, and meet the particular release profile characteristics that are required to achieve the administration regime involved.

The implant typically comprises a base composition which acts as a matrix to contain and hold the contents of the implant together. The base composition can, in turn, comprise one or more constituents. Examples of base compositions include polymers and copolymers of anhydrides, orthoester, lactic acid, glycolic acid, dioxonane, trimethylene carbonate, ε-caprolactone, phosphazene, andglyceryl monostearate.

In one embodiment the base composition for the matrix comprises a polyanydride, which can be synthesized via the dehydration of diacid molecules by melt condensation. Degradation times can be adjusted from days to years according to the hydrophobicity of the monomer selected. The materials degrade primarily by surface erosion and possess excellent in vivo compatibility. In one embodiment the polyanhydride is formed from sebasic acid and hexadecandioic acid (poly(SA-HDA anhydride). Wafer-like implants using this base composition have been approved for use in brain cancer, as Giadel®, by Guilford Pharmaceuticals.

The implant optionally can comprise erosion and biodegradation enhancers which facilitate the erosion of the matrix, the dissolution of the core composition, or the uptake of the core composition via metabolic processes. Particularly suitable erosion and biodegradation enhancers are biodegradable in biological fluids, and biocompatible. Hydrophilic constituents are typical, because they are capable of enhancing the erosion of the implant in the presence of biological fluids. For example, K. Juni et al., Chem. Pharm. Bull., 33, 1609 (1985) disclose that the release rate of bleomycin from polylactic acid microspheres is greatly enhanced by incorporating fatty acid esters into the microspheres. Other exemplary.hydrophilic constituents are described, for example, in Wade & Weller, Handbook of pharmaceutical Excipients (London: Pharmaceutical Press; Washington D.C.: American Pharmaceutical Ass'n 1995), and include the polyethylene glycols ("PEGs"), propylene glycol ("PG"), glycerin, and sorbitol.

Surfactants further enhance the erosion of the matrix and the release of the drug. Surfactants are generally capable of increasing the wettability and the solubility of the base composition in biological fluids, and thereby causing the disintegration and erosion of the implant. Surfactants can also help to break down the core composition matrix when, for example, the method of forming the dosage form has reduced the solubility of any of the constituents. Surfactants can also improve the uptake of the dosage forms into the bloodstream. Suitable surfactants include, for example, glyceryl based surfactants such as glyceryl monooleate and glyceryl monolaurate, polaxemers such as Pluronic F127, and polysorbates such as polyoxyethylene sorbitan monooleate ("Tween 80").

The implant could also include components that retard the rate at which the implant erodes or biodegrades (erosion and/or biodegradation retardants). Hydrophobic constituents are a particularly suitable class of components for retarding the rate at which the outer layer biodegrades. Suitable hydrophobic constituents are described, for example, in the Handbook of Pharmaceutical Excipients, the disclosure from which being hereby incorporated by reference. Exemplary hydrophobic constituents include peanut oil, olive oil, and castor oil.

Any proportions or types of constituents can be chosen that effectively achieve a desired release profile, and thereby carry out the prescribed administration regime. The most desirable base compositions generally release the drug substantially continuously, and biodegrade completely shortly after substantially all of the drug has been effectively released. The amount of drug included in the dosage forms is determined by the total amount of the drug to be administered, and the rate at which the drug is to be delivered. The total amount of the drug to be delivered is determined according to clinical requirements, and in keeping with the considerations that typically inform drug dosage determinations in other contexts. In one embodiment the implant comprises from zero to about 20 parts by weight erosion and/or biodegradation enhancers, from about 60 to about 100 parts by weight core base composition, and from about 1 to about 40 parts by weight of the dithiocarbamate and chemotherapeutic agent of the present invention. The surgical implant also can contain one or more other drugs having therapeutic efficacy in the intended applications, such as an antibiotic, an analgesic, or an anesthetic.

Modifications and variations of the present invention will be obvious to those skilled in the art from the foregoing detailed description of the invention. Such modifications and variations are intended to come with the scope of the appended claims.

What is claimed is:

1. A method of treating a tumor comprising administering an antiproliferative agent in combination with a effective amount of a N-substituted dithiocarbamate ester compound or a pharmaceutically acceptable salt thereof, wherein the N-substituted dithiocarbamate ester compound is defined by the following formula (I):

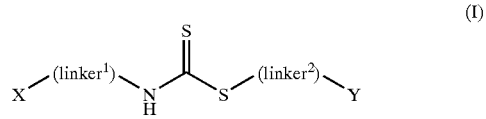

or its pharmaceutically acceptable salt, wherein:

a) X is oxolane;

b) Y is C(O)OR, c) R is hydrogen, alkyl, alkenyl, alkynyl, aryl, aralkyl, alkaryl, which can be optionally substituted with non-heterocyclic moieties; and d) linker¹ and linker² are independently alkyl, alkenyl, or alkynyl.

2. The method of claim 1 wherein the antiproliferative agent is a chemotherapeutic agent.

3. The method of claim 2 wherein the chemotherapeutic agent is 5-fluorouracil.

4. The method of claim 2 wherein the N-substituted dithiocarbamate ester compound is defined by the following structure (II):

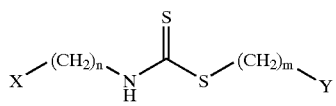

(II)

or its pharmaceutically acceptable salt, wherein:
a) n is 0, 1, 2, 3 or 4; and
b) m is 1–12.

5. The method of claim 2 wherein the N-substituted dithiocarbamate ester compound is 4-(tetrahydrofuran-2-ylmethylthiocarbamoylsulfanyl)-butyric acid methyl ester or its pharmaceutically acceptable salt, and the antiproliferative compound is 5-fluorouracil.

6. The method of claim 2 wherein the N-substituted dithiocarbamate ester compound is 4-(tetrahydrofuran-2-ylmethylthiocarbamoylsulfanyl)-butyric acid methyl ester, or its pharmaceutically acceptable salt.

7. The method of claim 2 wherein the N-substituted dithiocarbamate ester compound is selected from:

(Tetrahydrofuran-2-ylmethyl)dithiocarbamic acid alkyl ester;
(Tetrahydrofuran-2-ylmethyl)dithiocarbamic acid methyl ester;
(Tetrahydrofuran-2-ylmethylthiocarbamoylsulfanyl)acetic acid methyl ester;
3-(Tetrahydrofuran-2-ylmethylthiocarbamoylsulfanyl) propionic acid methyl ester;
4-(Tetrahydrofuran-2-ylmethylthiocarbamoylsulfanyl) butyric acid methyl ester;
6-(Tetrahydrofuran-2-ylmethylthiocarbamoylsulfanyl) hexanoic acid methyl ester;
4-(Tetrahydrofuran-2-ylmethylthiocarbamoylsulfanyl) butyric acid;
(Tetrahydrofuran-2-ylmethyl)dithiocarbamic acid 4-oxo-pentyl ester;
(Tetrahydrofuran-2-ylmethyl)dithiocarbamic acid 3-cyano-propyl ester;
2-Amino-3-(tetrahydrofuran-2-ylmethylthiocarbamoyl-sulfanyl)propionic acid;
2-Amino-4-(tetrahydrofuran-2-ylmethylthiocarbamoyl-sulfanyl)butyric acid;
(Tetrahydrofuran-2-ylmethyl)dithiocarbamic acid 3-carbamoyl-propyl ester;
(Tetrahydrofuran-2-ylmethyl)dithiocarbamic acid 3-dimethylcarbamoyl-propyl ester;
(Tetrahydrofuran-2-ylmethyl)dithiocarbamic acid benzyl ester;
(Tetrahydrofuran-2-ylmethyl)dithiocarbamic acid 2,4-dichloro-benzyl ester;
(Tetrahydrofuran-2-ylmethyl)dithiocarbamic acid phenyl ester;
(Tetrahydrofuran-2-ylmethyl)dithiocarbamic acid 4-chloro-phenyl ester;
(Tetrahydrofuran-2-ylmethyl)dithiocarbamic acid 2,4-difluoro-phenyl ester;
(Tetrahydrofuran-2-ylmethyl)dithiocarbamic acid tetrahydrothiophen-2-ylmethyl ester;
(Tetrahydrofuran-2-ylmethyl)dithiocarbamic acid thiophen-2-ylmethyl ester;
(Tetrahydrofuran-2-ylmethyl)dithiocarbamic acid tetrahydrothiophen-3-ylmethyl ester;
(Tetrahydrofuran-2-ylmethyl)dithiocarbamic acid thiophen-3-ylmethyl ester;
(Tetrahydrofuran-2-yl-methyl)dithio-carbamic acid 2,5-dichloro-thiophen-3-yl-methyl ester;
(Tetrahydrofuran-2-ylmethyl)dithiocarbamic acid 3,3-dimethyl-2-oxo-butyl ester;
(Tetrahydrofuran-2-yl-methyl)dithiocarbamic acid tetrahydrofuran-2-yl-methyl ester;
(Tetrahydrofuran-2-ylmethyl)dithiocarbamic acid furan-2-ylmethyl ester;
(Tetrahydrofuran-2-yl-methyl)dithiocarbamic acid tetrahydrofuran-3-yl-methyl ester;
(Tetrahydrofuran-2-yl-methyl)dithiocarbamic acid furan-3-ylmethyl ester;
(Tetrahydrofuran-2-yl-methyl)dithiocarbamic acid pyridin-2-ylmethyl ester;
(Tetrahydrofuran-2-yl-methyl)dithiocarbamic acid pyridin-3-ylmethyl ester;
4-((S)-Tetrahydrofuran-2-ylmethylthiocarbamoyl-sulfanyl) butyric acid methyl ester;
4-((R)-Tetrahydrofuran-2-ylmethylthiocarbamoyl-sulfanyl) butyric acid methyl ester;
4-(Tetrahydrofuran-2-yl-methylsulfanyllthio-carbonylamino)butyric acid ethyl ester;
4-(Tetrahydrofuran-3-ylmethylthiocarbamoylsulfanyl) butyric acid methyl ester;
4-(3S,4R-Dihydroxytetrahydrofuran-2S-ylmethylthiocarbamoylsulfanyl)butyric acid methyl ester;
4-(3R,4R-Dihydroxytetrahydrofuran-2R-ylmethylthiocarbamoylsulfanyl)butyric acid methyl ester;
4-(3R,4R-Dihydroxy-5R-methyltetrahydrofuran-2S-ylmethylthiocarbamoyl-sulfanyl)butyric acid methyl ester;

or a pharmaceutically acceptable salt thereof.

8. A method of treating a tumor comprising administering an effective amount of a N-substituted dithiocarbamate ester compound or a pharmaceutically acceptable salt thereof, wherein the N-substituted dithiocarbamate ester is defined by the following structure (I):

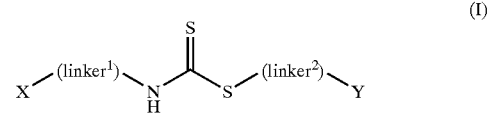

(I)

wherein:
a) X is oxolane;
b) Y is C(O)OR,
c) R is hydrogen, alkyl, alkenyl, alkynyl, aryl, aralkyl, alkaryl, which can be optionally substituted with non-heterocyclic moieties; and
d) linker$^1$ and linker$^2$ are independently alkyl, alkenyl, or alkynyl.

9. The method of claim 8 wherein the method further comprises administering an effective amount of 5-fluorouracil when the N-substituted dithiocarbamate ester compound is 4-(tetrahydrofuran-2-ylmethylthiocarbamoylsulfanyl)-butyric acid alkyl ester, or its pharmaceutically acceptable salt.

10. The method of claim 8 wherein the N-substituted dithiocarbamate ester compound is 4-(tetrahydrofuran-2-ylmethylthiocarbamoylsulfanyl)-butyric acid methyl ester, or its pharmaceutically acceptable salt.

11. The method of claim 8 wherein the N-substituted dithiocarbamate ester compound is selected from:

(Tetrahydrofuran-2-ylmethyl)dithiocarbamic acid alkyl ester;
(Tetrahydrofuran-2-ylmethyl)dithiocarbamic acid methyl ester;

(Tetrahydrofuran-2-ylmethylthiocarbamoylsulfanyl)acetic acid methyl ester;
3-(Tetrahydrofuran-2-ylmethylthiocarbamoylsulfanyl) propionic acid methyl ester;
4-(Tetrahydrofuran-2-ylmethylthiocarbamoylsulfanyl) butyric acid methyl ester;
6-(Tetrahydrofuran-2-ylmethylthiocarbamoylsulfanyl) hexanoic acid methyl ester;
4-(Tetrahydrofuran-2-ylmethylthiocarbamoylsulfanyl) butyric acid;
(Tetrahydrofuran-2-ylmethyl)dithiocarbamic acid 4-oxopentyl ester;
(Tetrahydrofuran-2-ylmethyl)dithiocarbamic acid 3-cyanopropyl ester;
2-Amino-3-(tetrahydrofuran-2-ylmethylthiocarbamoylsulfanyl)propionic acid;
2-Amino-4-(tetrahydrofuran-2-ylmethylthiocarbamoylsulfanyl)butyric acid;
(Tetrahydrofuran-2-ylmethyl)dithiocarbamic acid 3-carbamoyl-propyl ester;
(Tetrahydrofuran-2-ylmethyl)dithiocarbamic acid 3-dimethylcarbamoyl-propyl ester;
(Tetrahydrofuran-2-ylmethyl)dithiocarbarnic acid benzyl ester;
(Tetrahydrofuran-2-ylmethyl)dithiocarbamic acid 2,4-dichloro-benzyl ester;
(Tetrahydrofuran-2-ylmethyl)dithiocarbamic acid phenyl ester;
(Tetrahydrofuran-2-ylmethyl)dithiocarbamic acid 4-chlorophenyl ester;
(Tetrahydrofuran-2-ylmethyl)dithiocarbanic acid 2,4-difluoro-phenyl ester;
(Tetrahydrofuran-2-ylmethyl)dithiocarbamic acid tetrahydrothiophen-2-ylmethyl ester;
(Tetrahydrofuran-2-ylmethyl)dithiocarbamic acid thiophen-2-ylmethyl ester;
(Tetrahydrofuran-2-ylmethyl)dithiocarbamic acid tetrahydrothiophen-3-ylmethyl ester;
(Tetrahydrofuran-2-ylmethyl)dithiocarbamic acid thiophen-3-ylmethyl ester;
(Tetrahydrofuran-2-yl-methyl)dithio-carbamic acid 2,5-dichloro-thiophen-3-yl-methyl ester;
(Tetrahydrofuran-2-ylmethyl)dithiocarbamic acid 3,3-dimethyl-2-oxo-butyl ester;
(Tetrahydrofuran-2-yl-methyl)dithiocarbamic acid tetrahydrofuran-2-yl-methyl ester;
(Tetrahydrofuran-2-ylmethyl)dithiocarbamic acid furan-2-ylmethyl ester;
(Tetrahydrofuran-2-yl-methyl)dithiocarbamic acid tetrahydrofuran-3-yl-methyl ester;
(Tetrahydrofuran-2-yl-methyl)dithiocarbamic acid furan-3-ylmethyl ester;
(Tetrahydrofuran-2-yl-methyl)dithiocarbamic acid pyridin-2-ylmethyl ester;
(Tetrahydrofuran-2-yl-methyl)dithiocarbamic acid pyridin-3-ylmethyl ester;
4-((S)-Tetrahydrofuran-2-ylmethylthiocarbamoyl-sulfanyl) butyric acid methyl ester;
4-((R)-Tetrahydrofuran-2-ylmethylthiocarbamoyl-sulfanyl) butyric acid methyl ester;
4-(Tetrahydrofuran-2-yl-methylsulfanyllthio-carbonylamino)butyric acid ethyl ester;
4-(Tetrahydrofuran-3-ylmethylthiocarbamoylsulfanyl) butyric acid methyl ester;
4-(3S,4R-Dihydroxytetrahydrofuran-2S-ylmethylthiocarbamoylsulfanyl)butyric acid methyl ester;
4-(3R,4R-Dihydroxytetrahydrofuran-2R-ylmethylthiocarbamoylsulfanyl)butyric acid methyl ester;
4-(3R,4R-Dihydroxy-5R-methyltetrahydrofuran-2S-ylmethylthiocarbamoyl-sulfanyl)butyric acid methyl ester;

or a pharmaceutically acceptable salt thereof.

12. A method of treating a VCAM-1 mediated condition comprising administering an effective amount of a N-substituted dithiocarbamate ester compound or a pharmaceutically acceptable salt thereof, wherein the N-substituted dithiocarbamate ester is defined by the following structure (I):

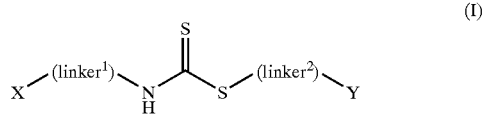

wherein:
a) X is oxolane;
b) Y is C(O)OR,
c) R is hydrogen, alkyl, alkenyl, alkynyl, aryl, aralkyl, alkaryl, which can be optionally substituted with non-heterocyclic moieties; and
d) linker$^1$ and linker$^2$ are independently alkyl, alkenyl, or alkynyl.

13. The method of claim 12 wherein the N-substituted dithiocarbamate ester compound is defined by the following structure (II):

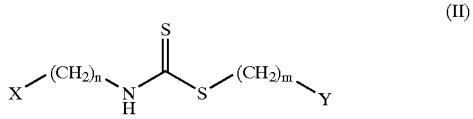

or its pharmaceutically acceptable salt, wherein:
a) n is 1–3; and
b) m is 1–6.

14. The method of claim 12 wherein the N-substituted dithiocarbamate ester compound is 4-(tetrahydrofuran-2-ylmethylthiocarbamoylsulfanyl)-butyric acid alkyl ester, or its pharmaceutically acceptable salt.

15. The method of claim 12 wherein the N-substituted dithiocarbamate ester compound is 4-(tetrahydrofuran-2-ylmethylthiocarbamoylsulfanyl)-butyric acid methyl ester, or its pharmaceutically acceptable salt.

16. The method of claim 12 wherein the N-substituted dithiocarbamate ester compound is selected from:

(Tetrahydrofuran-2-ylmethyl)dithiocarbamic acid alkyl ester;
(Tetrahydrofuran-2-ylmethyl)dithiocarbamic acid methyl ester;
(Tetrahydrofuran-2-ylmethylthiocarbamoylsulfanyl)acetic acid methyl ester;
3-(Tetrahydrofuran-2-ylmethylthiocarbamoylsulfanyl) propionic acid methyl ester;
4-(Tetrahydrofuran-2-ylmethylthiocarbamoylsulfanyl) butyric acid methyl ester;
6-(Tetrahydrofuran-2-ylmethylthiocarbamoylsulfanyl) hexanoic acid methyl ester;
4-(Tetrahydrofuran-2-ylmethylthiocarbamoylsulfanyl) butyric acid;
(Tetrahydrofuran-2-ylmethyl)dithiocarbamic acid 4-oxopentyl ester;

(Tetrahydrofuran-2-ylmethyl)dithiocarbamic acid 3-cyano-propyl ester;
2-Amino-3-(tetrahydrofuran-2-ylmethylthiocarbamoyl-sulfanyl)propionic acid;
2-Amino-4-(tetrahydrofuran-2-ylmethylthiocarbamoyl-sulfanyl)butyric acid;
(Tetrahydrofuran-2-ylmethyl)dithiocarbamic acid 3-carbamoyl-propyl ester;
(Tetrahydrofuran-2-ylmethyl)dithiocarbamic acid 3-dimethylcarbamoyl-propyl ester;
(Tetrahydrofuran-2-ylmethyl)dithiocarbamic acid benzyl ester;
(Tetrahydrofuran-2-ylmethyl)dithiocarbamic acid 2,4-dichloro-benzyl ester;
(Tetrahydrofuran-2-ylmethyl)dithiocarbamic acid phenyl ester;
(Tetrahydrofuran-2-ylmethyl)dithiocarbamic acid 4-chloro-phenyl ester;
(Tetrahydrofuran-2-ylmethyl)dithiocarbamic acid 2,4-difluoro-phenyl ester;
(Tetrahydrofuran-2-ylmethyl)dithiocarbamic acid tetrahydrothiophen-2-ylmethyl ester;
(Tetrahydrofuran-2-ylmethyl)dithiocarbamic acid thiophen-2-ylmethyl ester;
(Tetrahydrofuran-2-ylmethyl)dithiocarbamic acid tetrahydrothiophen-3-ylmethyl ester;
(Tetrahydrofuran-2-ylmethyl)dithiocarbamic acid thiophen-3-ylmethyl ester;
(Tetrahydrofuran-2-yl-methyl)dithio-carbamic acid 2,5-dichloro-thiophen-3-yl-methyl ester;
(Tetrahydrofuran-2-ylmethyl)dithiocarbamic acid 3,3-dimethyl-2-oxo-butyl ester;
(Tetrahydrofuran-2-yl-methyl)dithiocarbamic acid tetrahydrofuran-2-yl-methyl ester;
(Tetrahydrofuran-2-ylmethyl)dithiocarbamic acid furan-2-ylmethyl ester;
(Tetrahydrofuran-2-yl-methyl)dithiocarbamic acid tetrahydrofuran-3-yl-methyl ester;
(Tetrahydrofuran-2-yl-methyl)dithiocarbamic acid furan-3-ylmethyl ester;
(Tetrahydrofuran-2-yl-methyl)dithiocarbamic acid pyridin-2-ylmethyl ester;
(Tetrahydrofuran-2-yl-methyl)dithiocarbamic acid pyridin-3-ylmethyl ester;
4-((S)-Tetrahydrofuran-2-ylmethylthiocarbamoyl-sulfanyl)butyric acid methyl ester;
4-((R)-Tetrahydrofuran-2-ylmethylthiocarbamoyl-sulfanyl)butyric acid methyl ester;
4-(Tetrahydrofuran-2-yl-methylsulfanyl]thio-carbonylamino)butyric acid ethyl ester;
4-(Tetrahydrofuran-3-ylmethylthiocarbamoylsulfanyl)butyric acid methyl ester;
4-(3S,4R-Dihydroxytetrahydrofuran-2S-ylmethylthiocarbamoylsulfanyl)butyric acid methyl ester;
4-(3R,4R-Dihydroxytetrahydrofuran-2R-ylmethylthiocarbamoylsulfanyl)butyric acid methyl ester;
4-(3R,4R-Dihydroxy-5R-methyltetrahydrofuran-2S-ylmethylthiocarbamoyl-sulfanyl)butyric acid methyl ester;

or a pharmaceutically acceptable salt thereof.

17. An N-substituted dithiocarbamate ester compound of the formula (II):

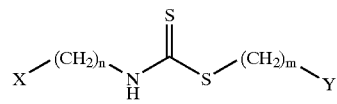

or its pharmaceutically acceptable salt, wherein:
a) X is oxolane;
b) Y is C(O)OR,
c) n and m are independently 1, 2, 3, 4, 5, 6, 7, 8, 9, 10, 11 or 12;
d) and R is hydrogen, alkyl, alkenyl, alkynyl, aryl, aralkyl, alkaryl, which can be optionally substituted with non-heterocyclic moieties.

18. The compound of claim 17 wherein n is 1.
19. The compound of claim 17 wherein m is 1,2, 3, 4 or 5.
20. A compound of the structure:

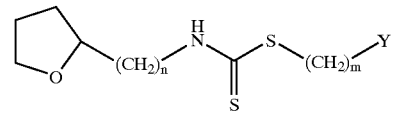

or its pharmaceutically acceptable salt, wherein:
a) Y is C(O)OR;
b) R is hydrogen, lower alkyl or substituted lower alkyl;
c) n is 1–12; and
d) m is 1–12.

21. The compound

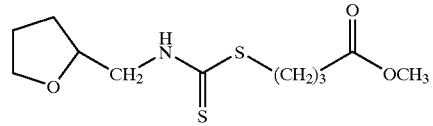

or its pharmaceutically acceptable salt.

22. A compound of the formula:

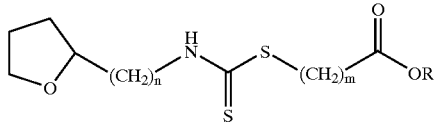

or its pharmaceutically acceptable salt, wherein:
a) R is H or independently substituted lower alkyl; and
b) n and m are independently 1, 2, 3, 4, 5, 6, 7, 8 or 10.

23. The compound of claim 22 wherein R is lower alkyl and n and m are independently selected from 1, 2, 3 or 4.

24. A compound selected from:

(Tetrahydrofuran-2-ylmethyl)dithiocarbamic acid alkyl ester;
(Tetrahydrofuran-2-ylmethyl)dithiocarbamic acid methyl ester;
(Tetrahydrofuran-2-ylmethylthiocarbamoylsulfanyl)acetic acid methyl ester;
3-(Tetrahydrofuran-2-ylmethylthiocarbamoylsulfanyl)-propionic acid methyl ester;
4-(Tetrahydrofuran-2-ylmethylthiocarbamoylsulfanyl)-butyric acid methyl ester;

6-(Tetrahydrofuran-2-ylmethylthiocarbamoyl-sulfanyl) hexanoic acid methyl ester;
4-(Tetrahydrofuran-2-ylmethylthiocarbamoylsulfanyl)-butyric acid;
(Tetrahydrofuran-2-ylmethyl)dithiocarbamic acid 4-oxo-pentyl ester; and
(Tetrahydrofuran-2-ylmethyl)dithiocarbamic acid 3-cyano-propyl ester;
2-Amino-3-(tetrahydrofuran-2-ylmethylthiocarbamoyl-sulfanyl)propionic acid;
2-Amino-4-(tetrahydrofuran-2-ylmethylthiocarbamoyl-sulfanyl)butyric acid;
(Tetrahydrofuran-2-ylmethyl)dithiocarbamic acid 3-carbamoyl-propyl ester;
(Tetrahydrofuran-2-ylmethyl)dithiocarbamic acid 3-dimethylcarbamoyl-propyl ester;
(Tetrahydrofuran-2-ylmethyl)dithiocarbamic acid benzyl ester;
(Tetrahydrofuran-2-ylmethyl)dithiocarbamic acid 2,4-dichloro-benzyl ester;
(Tetrahydrofuran-2-ylmethyl)dithiocarbamic acid phenyl ester;
(Tetrahydrofuran-2-ylmethyl)dithiocarbamic acid 4-chloro-phenyl ester;
(Tetrahydrofuran-2-ylmethyl)dithiocarbamic acid 2,4-difluoro-phenyl ester;
(Tetrahydrofuran-2-ylmethyl)dithiocarbamic acid tetrahydrothiophen-2-ylmethyl ester;
(Tetrahydrofuran-2-ylmethyl)dithiocarbamic acid thiophen-2-ylmethyl ester;
(Tetrahydrofuran-2-ylmethyl)dithiocarbamic acid tetrahydrothiophen-3-ylmethyl ester;
(Tetrahydrofuran-2-ylmethyl)dithiocarbamic acid thiophen-3-ylmethyl ester;
(Tetrahydrofuran-2-ylmethyl)dithiocarbamic acid 2,5-dichloro-thiophen-3-ylmethyl ester;
(Tetrahydrofuran-2-ylmethyl)dithiocarbamic acid 3,3-dimethyl-2-oxo-butyl ester;
(Tetrahydrofuran-2-ylmethyl)dithiocarbamic acid tetrahydrofuran-2-ylmethyl ester;
(Tetrahydrofuran-2-ylmethyl)dithiocarbamic acid furan-2-ylmethyl ester;
(Tetrahydrofuran-2-ylmethyl)dithiocarbamic acid tetrahydrofuran-3-ylmethyl ester;
(Tetrahydrofuran-2-ylmethyl)dithiocarbamic acid furan-3-ylmethyl ester;
(Tetrahydrofuran-2-ylmethyl)dithiocarbamic acid pyridin-2-ylmethyl ester;
(Tetrahydrofuran-2-ylmethyl)dithiocarbamic acid pyridin-3-ylmethyl ester;
4-((S)-Tetrahydrofuran-2-ylmethylthiocarbamoyl-sulfanyl) butyric acid methyl ester;
4-((R)-Tetrahydrofuran-2-ylmethylthiocarbamoyl-sulfanyl) butyric acid methyl ester;
4-(Tetrahydrofuran-2-ylmethylsulfanyllthio-carbonylamino)butyric acid ethyl ester;
4-(Tetrahydrofuran-3-ylmethylthiocarbamoylsulfanyl) butyric acid methyl ester;
4-(3S,4R-Dihydroxytetrahydrofuran-2S-ylmethylthiocarbamoylsulfanyl)butyric acid methyl ester;
4-(3R,4R-Dihydroxytetrahydrofuran-2R-ylmethylthiocarbamoylsulfanyl)butyric acid methyl ester; and
4-(3R,4R-Dihydroxy-5R-methyltetrahydrofuran-2S-ylmethylthiocarbamoylsulfanyl)-butyric acid methyl ester;

or its pharmaceutically acceptable salt, thereof.

25. A pharmaceutical composition comprising an effective treatment amount of an N-substituted dithiocarbamate ester compound of the formula (II):

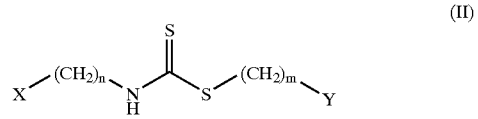

(II)

or its pharmaceutically acceptable salt together with a pharmaceutically acceptable carrier, wherein:

a) X is oxolane;
b) Y is C(O)OR;
c) n and m are independently 1, 2, 3, 4, 5, 6, 7, 8, 9, 10, 11 or 12; and
d) R is hydrogen, alkyl, alkenyl, alkynyl, aryl, aralkyl, alkaryl, which can be optionally substituted with non-heterocyclic moieties.

26. The pharmaceutical composition of claim 25 wherein n is 1.

27. The pharmaceutical composition of claim 25 wherein m is 1, 2, 3, 4 or 5.

28. A pharmaceutical composition comprising an effective treatment amount of an N-substituted dithiocarbamate ester compound of the structure:

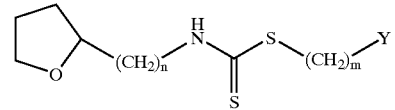

or its pharmaceutically acceptable salt together with a pharmaceutically acceptable carrier, wherein:

a) Y is C(O)OR,
b) R is hydrogen, alkyl, alkenyl, alkynyl, aryl, aralkyl, alkaryl, which can be optionally substituted with non-heterocyclic moieties; and
c) n and m are independently 1, 2, 3, 4, 5, 6, 7, 8, 9, 10, 11 or 12.

29. A pharmaceutical composition comprising an effective treatment amount of an N-substituted dithiocarbamate ester compound of the structure:

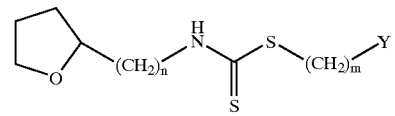

or its pharmaceutically acceptable salt together with a pharmaceutically acceptable carrier, wherein:

a) Y is C(O)OR,
b) R is hydrogen, alkyl, alkenyl, alkynyl, aryl, aralkyl, alkaryl, which can be optionally substituted with non-heterocyclic moieties;
c) n is 1–3; and
d) m is 1–6.

30. A pharmaceutical composition comprising an effective treatment amount of an N-substituted dithiocarbamate ester compound of the structure:

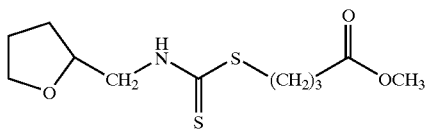

or its pharmaceutically acceptable salt together with a pharmaceutically acceptable carrier.

31. A pharmaceutical composition comprising an effective treatment amount of an N-substituted dithiocarbamate ester compound of the structure:

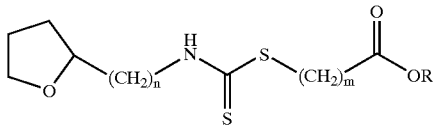

or its pharmaceutically acceptable salt together with a pharmaceutically acceptable carrier, wherein:
  a) R is H or independently substituted lower alkyl; and
  b) n and m are independently 1, 2, 3, 4, 5, 6, 7, 8 or 10.

32. The pharmaceutical composition of claim 31, wherein R is lower alkyl and n and m are independently selected from 1, 2, 3 or 4.

33. A pharmaceutical composition comprising an effective treatment amount of an N-substituted dithiocarbamate selected from:

(Tetrahydrofuran-2-ylmethyl)dithiocarbamic acid alkyl ester;
(Tetrahydrofuran-2-ylmethyl)dithiocarbamic acid methyl ester;
(Tetrahydrofuran-2-ylmethylthiocarbamoylsulfanyl)acetic acid methyl ester;
3-(Tetrahydrofuran-2-ylmethylthiocarbamoylsulfanyl)-propionic acid methyl ester;
4-(Tetrahydrofuran-2-ylmethylthiocarbamoylsulfanyl)-butyric acid methyl ester;
6-(Tetrahydrofuran-2-ylmethylthiocarbamoyl-sulfanyl) hexanoic acid methyl ester;
4-(Tetrahydrofuran-2-ylmethylthiocarbamoylsulfanyl)-butyric acid;
(Tetrahydrofuran-2-ylmethyl)dithiocarbamic acid 4-oxo-pentyl ester; and
(Tetrahydrofuran-2-ylmethyl)dithiocarbamic acid 3-cyano-propyl ester;
2-Amino-3-(tetrahydrofuran-2-ylmethylthiocarbamoyl-sulfanyl)propionic acid;
2-Amino-4-(tetrahydrofuran-2-ylmethylthiocarbamoyl-sulfanyl)butyric acid;
(Tetrahydrofuran-2-ylmethyl)dithiocarbamic acid 3-carbamoyl-propyl ester;
(Tetrahydrofuran-2-ylmethyl)dithiocarbamic acid 3-dimethylcarbamoyl-propyl ester;
(Tetrahydrofuran-2-ylmethyl)dithiocarbamic acid benzyl ester;
(Tetrahydrofuran-2-ylmethyl)dithiocarbamic acid 2,4-dichloro-benzyl ester;
(Tetrahydrofuran-2-ylmethyl)dithiocarbamic acid phenyl ester;
(Tetrahydrofuran-2-ylmethyl)dithiocarbamic acid 4-chloro-phenyl ester;
(Tetrahydrofuran-2-ylmethyl)dithiocarbamic acid 2,4-difluoro-phenyl ester;
(Tetrahydrofuran-2-ylmethyl)dithiocarbamic acid tetrahydrothiophen-2-ylmethyl ester;
(Tetrahydrofuran-2-ylmethyl)dithiocarbamic acid thiophen-2-ylmethyl ester;
(Tetrahydrofuran-2-ylmethyl)dithiocarbamic acid tetrahydrothiophen-3-ylmethyl ester;
(Tetrahydrofuran-2-ylmethyl)dithiocarbamic acid thiophen-3-ylmethyl ester;
(Tetrahydrofuran-2-ylmethyl)dithiocarbamic acid 2,5-dichloro-thiophen-3-ylmethyl ester;
(Tetrahydrofuran-2-ylmethyl)dithiocarbamic acid 3,3-dimethyl-2-oxo-butyl ester;
(Tetrahydrofuran-2-ylmethyl)dithiocarbamic acid tetrahydrofuran-2-ylmethyl ester;
(Tetrahydrofuran-2-ylmethyl)dithiocarbamic acid furan-2-ylmethyl ester;
(Tetrahydrofuran-2-ylmethyl)dithiocarbamic acid tetrahydrofuran-3-ylmethyl ester;
(Tetrahydrofuran-2-ylmethyl)dithiocarbamic acid furan-3-ylmethyl ester;
(Tetrahydrofuran-2-ylmethyl)dithiocarbamic acid pyridin-2-ylmethyl ester;
(Tetrahydrofuran-2-ylmethyl)dithiocarbamic acid pyridin-3-ylmethyl ester;
4-((S)-Tetrahydrofuran-2-ylmethylthiocarbamoyl-sulfanyl) butyric acid methyl ester;
4-((R)-Tetrahydrofuran-2-ylmethylthiocarbamoyl-sulfanyl) butyric acid methyl ester;
4-(Tetrahydrofuran-2-ylmethylsulfanyllthio-carbonylamino)butyric acid ethyl ester;
4-(Tetrahydrofuran-3-ylmethylthiocarbamoylsulfanyl) butyric acid methyl ester;
4-(3S,4R-Dihydroxytetrahydrofuran-2S-ylmethylthiocarbamoylsulfanyl)butyric acid methyl ester;
4-(3R,4R-Dihydroxytetrahydrofuran-2R-ylmethylthiocarbamoylsulfanyl)butyric acid methyl ester; and
4-(3R,4R-Dihydroxy-5R-methyltetrahydrofuran-2S-ylmethylthiocarbamoylsulfanyl)-butyric acid methyl ester;

or its pharmaceutically acceptable salt, together with a pharmaceutically acceptable carrier.

34. The pharmaceutical composition composition of any of the preceding claims 25, 26, 27, 28, 29, 30, 31, 32, or 33, wherein the said compound is in the form of a dosage unit.

35. The pharmaceutical composition as described in claim 34, wherein the dosage unit contains 10 to 1500 mg of said compound.

36. The pharmaceutical composition as described in claim 34, wherein said dosage unit is a tablet or capsule.

37. The pharmaceutical composition as described in claim 35, wherein said dosage unit is a tablet or capsule.

38. The method of claim 4 wherein n is 1–3, and m is 1–12.

39. The method of claim 4 wherein n is 1–3, and m is 1–6.

40. The method of claim 4 wherein n is 1 and m is 3–5.

41. The method of claim 13 wherein n is 1 and m is 3–5.

42. The compound of claim 17 wherein n is 1–3, and m is 1–12.

43. The compound of claim 17 wherein n is 1–3, and m is 1–6.

44. The compound of claim 17 wherein n is 1 and m is 3–5.

45. The compound of claim 20 wherein n is 1–3, and m is 1–12.

46. The compound of claim 20 wherein n is 1–3, and m is 1–6.

47. The compound of claim 20 wherein n is 1 and m is 3–5.

48. The compound of claim 22 wherein n is 1–3, and m is 1–12.

49. The compound of claim 22 wherein n is 1–3, and m is 1–6.

50. The compound of claim 22 wherein n is 1 and m is 3–5.

51. The composition of claim 25 wherein n is 1–3, and m is 1–12.

52. The composition of claim 25 wherein n is 1–3, and m is 1–6.

53. The composition of claim 25 wherein n is 1 and m is 3–5.

54. The composition of claim 28 wherein n is 1–3, and m is 1–12.

55. The composition of claim 28 wherein n is 1–3, and m is 1–6.

56. The composition of claim 28 wherein n is 1 and m is 3–5.

57. The composition of claim 31 wherein n is 1–3, and m is 1–12.

58. The composition of claim 31 wherein n is 1–3, and m is 1–6.

59. The composition of claim 31 wherein n is 1 and m is 3–5.

* * * * *